(12) United States Patent
Toda et al.

(10) Patent No.: US 10,012,959 B2
(45) Date of Patent: Jul. 3, 2018

(54) LIGHTING DEVICE AND LIGHTING SYSTEM

(71) Applicant: Panasonic Intellectual Property Management Co., Ltd., Osaka-shi, Osaka (JP)

(72) Inventors: Naohiro Toda, Chiba (JP); Kazuhiro Hatta, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 113 days.

(21) Appl. No.: 15/216,587

(22) Filed: Jul. 21, 2016

(65) Prior Publication Data

US 2017/0031324 A1 Feb. 2, 2017

(30) Foreign Application Priority Data

Jul. 29, 2015 (JP) .................................. 2015-150135

(51) Int. Cl.
| | |
|---|---|
| *G04G 11/00* | (2006.01) |
| *G04G 13/02* | (2006.01) |
| *H05B 37/02* | (2006.01) |
| *A61B 5/00* | (2006.01) |

(52) U.S. Cl.
CPC ............ *G04G 11/00* (2013.01); *A61B 5/4809* (2013.01); *G04G 13/02* (2013.01); *H05B 37/02* (2013.01); *H05B 37/0227* (2013.01); *Y02B 20/44* (2013.01)

(58) Field of Classification Search
CPC ........ G04C 19/00; G04C 19/02; G04G 11/00; G04G 13/00; G04G 13/02; A61B 5/047; A61B 5/08; A61B 5/682; H05B 37/0227; H05B 37/02
See application file for complete search history.

(56) References Cited

U.S. PATENT DOCUMENTS

| | | | | |
|---|---|---|---|---|
| 4,228,806 A * | 10/1980 | Lidow | .................. | A61B 5/0476 368/12 |
| 5,008,865 A * | 4/1991 | Shaffer | .................. | G04G 11/00 315/194 |
| 6,236,622 B1 * | 5/2001 | Blackman | .............. | G04B 47/00 362/253 |
| 6,888,779 B2 * | 5/2005 | Mollicone | ............. | A61M 21/00 368/10 |
| 7,492,672 B2 * | 2/2009 | Cuisinier | ............. | G04G 13/023 368/262 |
| 7,956,756 B2 * | 6/2011 | Kubey | .................. | A61B 3/113 340/573.1 |

(Continued)

FOREIGN PATENT DOCUMENTS

| | | |
|---|---|---|
| JP | 4-264289 A | 9/1992 |
| JP | 8-146168 A | 6/1996 |

(Continued)

*Primary Examiner* — Vit W Miska
(74) *Attorney, Agent, or Firm* — McDermott Will & Emery LLP

(57) ABSTRACT

A lighting device includes: an illuminator which emits illumination light; a clock which measures time; a receiver which receives input of a set time from a user; a sensor which detects whether an eye of the user is open; and a controller which controls, at or after the set time, the illuminator, based on a result of the detection by the sensor.

10 Claims, 23 Drawing Sheets

(56) References Cited

U.S. PATENT DOCUMENTS

| | | | | |
|---|---|---|---|---|
| 8,259,535 B2* | 9/2012 | Sandu | ............... | A61M 21/00 |
| | | | | 362/253 |
| 8,562,659 B2* | 10/2013 | Wells | ............... | A61B 5/6821 |
| | | | | 607/88 |
| 8,867,318 B2* | 10/2014 | Suen | ............... | G04G 11/00 |
| | | | | 368/241 |
| 9,310,779 B2* | 4/2016 | Huh | ............... | G04G 13/021 |
| 2003/0062856 A1* | 4/2003 | Yano | ............... | H05B 39/044 |
| | | | | 315/291 |
| 2007/0002692 A1* | 1/2007 | Van Brunt | ............ | G04G 13/021 |
| | | | | 368/79 |
| 2010/0254571 A1* | 10/2010 | Matsuura | ............ | G06K 9/00281 |
| | | | | 382/103 |
| 2014/0009282 A1* | 1/2014 | Baloa Welzien | ...... | G04G 11/00 |
| | | | | 340/539.11 |
| 2015/0097490 A1 | 4/2015 | Okuya et al. | | |

FOREIGN PATENT DOCUMENTS

| | | |
|---|---|---|
| JP | 2007-198972 A | 8/2007 |
| JP | 2008-157774 A | 7/2008 |
| JP | 2011-092271 A | 5/2011 |
| JP | 2015-069781 A | 4/2015 |

* cited by examiner

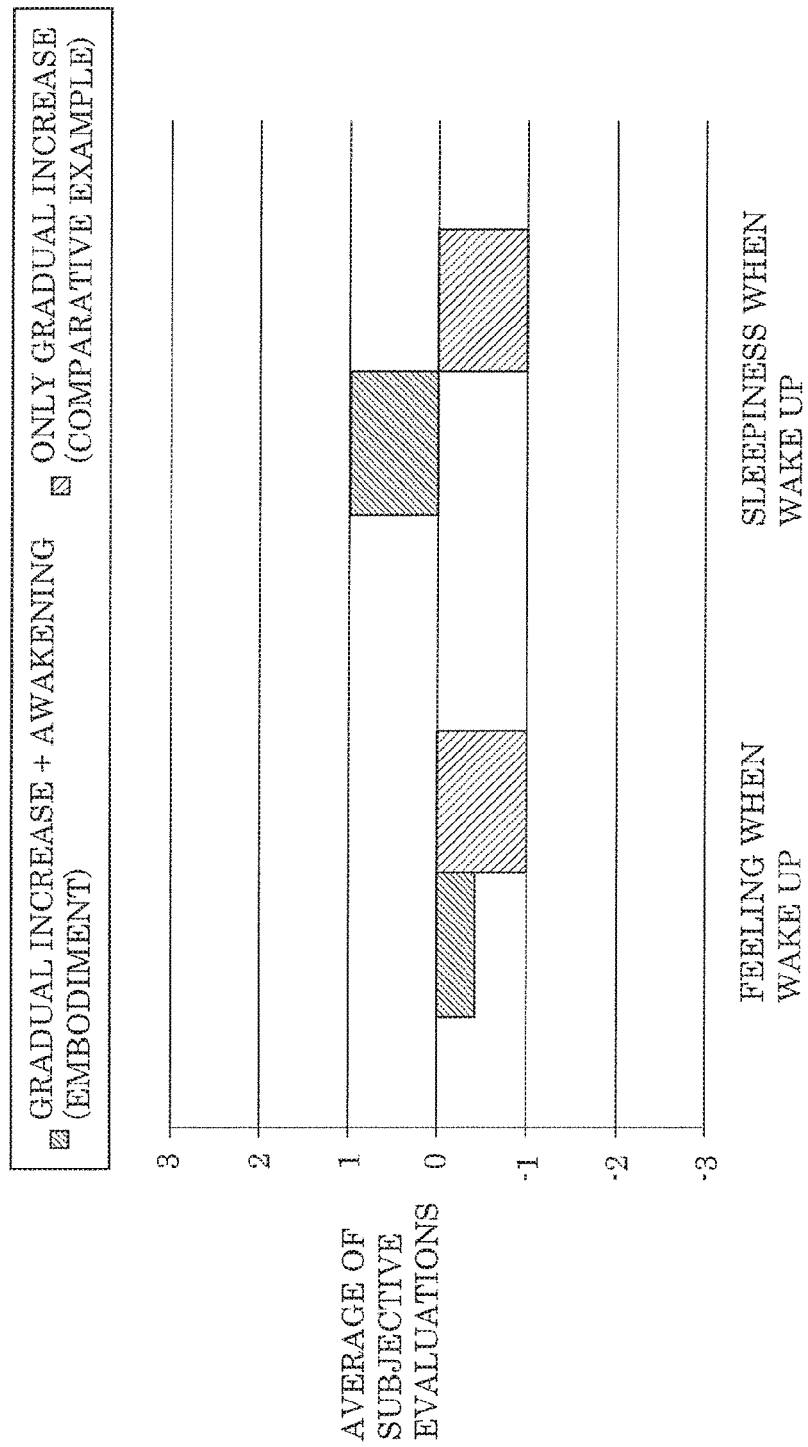

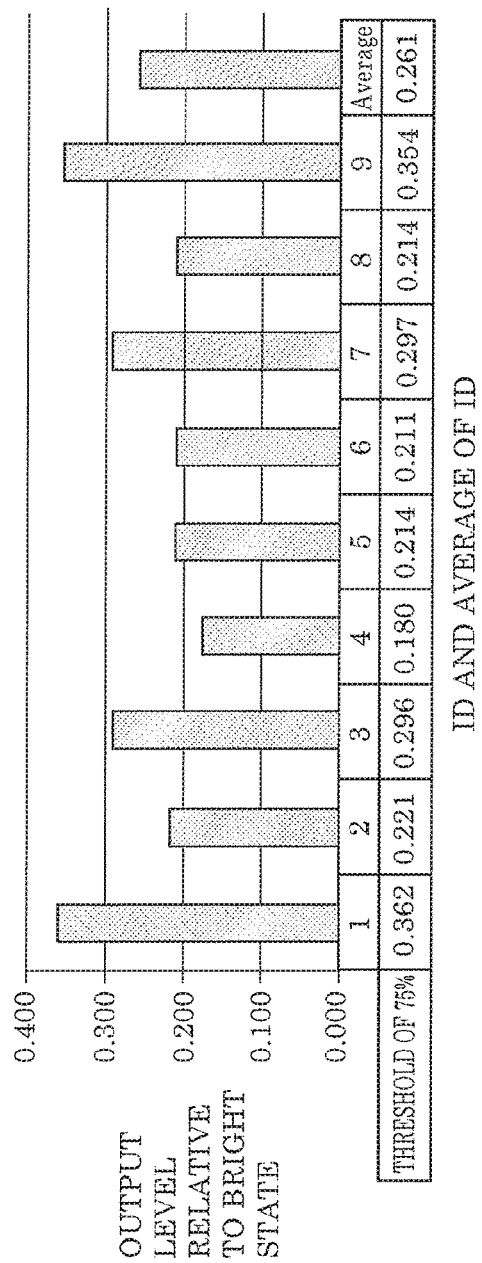

LIGHTING DEVICE AND LIGHTING SYSTEM

CROSS REFERENCE TO RELATED APPLICATION

This application claims the benefit of priority of Japanese Patent Application Number 2015-150135 filed on Jul. 29, 2015, the entire content of which is hereby incorporated by reference.

BACKGROUND

1. Technical Field

The present disclosure relates to lighting devices and lighting systems.

2. Description of the Related Art

A conventional lighting device which creates, in a house, light environment mainly for a resident to wake up pleasantly has been known. For example, Japanese Unexamined Patent Application Publication No. H04-264289 discloses an alarm device which starts to gradually increase an amount of light at a time which is a certain time period earlier than a designated wake-up time.

The alarm device disclosed in Japanese Unexamined Patent Application Publication No. H04-264289, however, cannot wake up a person still sleeping after the designated wake-up time (i.e., a person who has gone back to sleep). To address this, Japanese Unexamined Patent Application Publication No. 2008-157774 discloses an alarm lighting device which intermittently gives light and sound stimuli at or after a designated wake-up time in order to awaken a person still sleeping after the designated wake-up time.

SUMMARY

However, merely intermittently giving light and sound stimuli does not necessarily result in pleasantly waking up a person. In order to pleasantly wake up a user, making the user feel good and reducing the user's sleepiness may be both achieved when the user wakes up.

In view of this, the present disclosure provides a lighting device and a lighting system which pleasantly wake up a user.

In order to pleasantly wake up a user, a lighting device according to an aspect of the present disclosure includes: an illuminator which emits illumination light; a clock which measures time; a receiver which receives input of a set time from a user; a detector which detects whether an eye of the user is open; and a controller which controls, at or after the set time, a dimming level of the illuminator, in accordance with a control pattern based on a result of the detection by the detector.

Furthermore, a lighting system according to an aspect of the present disclosure includes: a lighting device which includes an illuminator which emits illumination light; a control device which controls the lighting device; and a detector which detects whether an eye of a user is open, wherein the control device includes: a clock which measures time; a receiver which receives input of a set time from the user; and a controller which controls, at or after the set time, a dimming level of the illuminator, in accordance with a control pattern based on a result of the detection by the detector.

The lighting device and so forth according to the present disclosure can wake up a user pleasantly.

BRIEF DESCRIPTION OF DRAWINGS

The figures depict one or more implementations in accordance with the present teaching, by way of examples only, not by way of limitations. In the figures, like reference numerals refer to the same or similar elements.

FIG. 13A illustrates results of experiments of wake-up control according to Embodiment 1;

FIG. 13B illustrates results of experiments for obtaining an appropriate value of a dimming level at a second time according to Embodiment 1;

DETAILED DESCRIPTION OF THE EMBODIMENTS

The following describes in detail lighting devices and lighting systems according to embodiments of the present disclosure, with reference to the drawings. The embodiments described below each show a specific example. The numerical values, shapes, materials, elements, the arrangement and connection of the elements, steps, the processing order of the steps, and the like shown in the following embodiments are mere examples, and are not intended to limit the present disclosure. Therefore, among the elements in the following embodiments, elements not recited in any of the independent claims defining the most generic part of the present disclosure are described as arbitrary elements.

Embodiment 1

Outline

Figure 1:
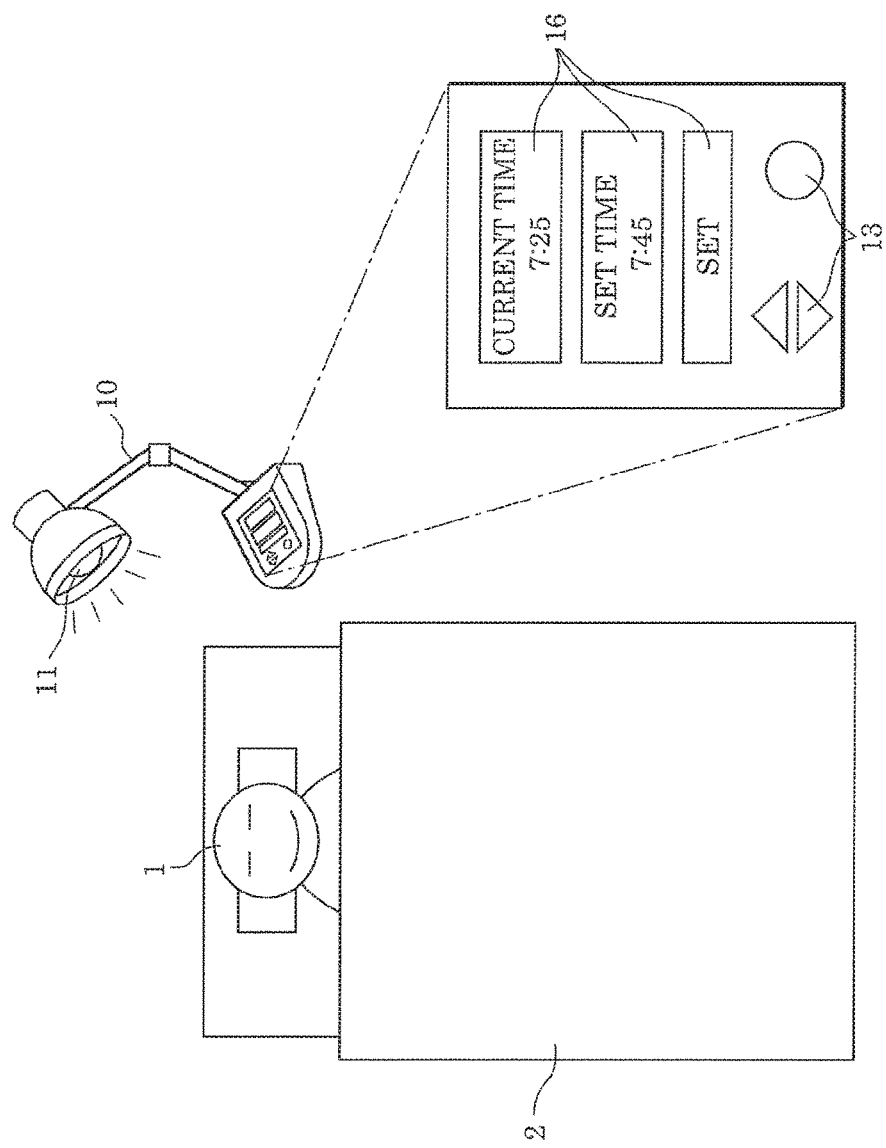
FIG. 1 is a schematic diagram illustrating a lighting device according to Embodiment 1 and a use environment of the lighting device.

First, a description of the outline of a lighting device according to the present embodiment is given with reference to FIG. 1. FIG. 1 is a schematic diagram illustrating lighting device 10 according to the present embodiment and a use environment of lighting device 10.

Lighting device 10 performs wake-up control for pleasantly waking up user 1 sleeping on bed 2. Wake-up control is to control a dimming level (light output) of illuminator 11 of lighting device 10. In the present embodiment, as illustrated in FIG. 1, lighting device 10 is a reading-lamp (desk-lamp) lighting device, and is placed near bed 2. Specifically, lighting device 10 is placed at the bedside of user 1, and illuminates the face of user 1.

User 1 inputs, for instance, a set time via input unit 13 of lighting device 10. A set time is a time at which user 1 wishes to wake up. The input set time is displayed on display 16 of lighting device 10, for example.

Lighting device 10 starts wake-up control at a start time prior to the input set time. Specifically, lighting device 10 performs gradual increase control from the start time to the set time, and performs awakening control after the set time. A detailed description of the controls is later given.
[Configuration of Lighting Device]

Figure 2:
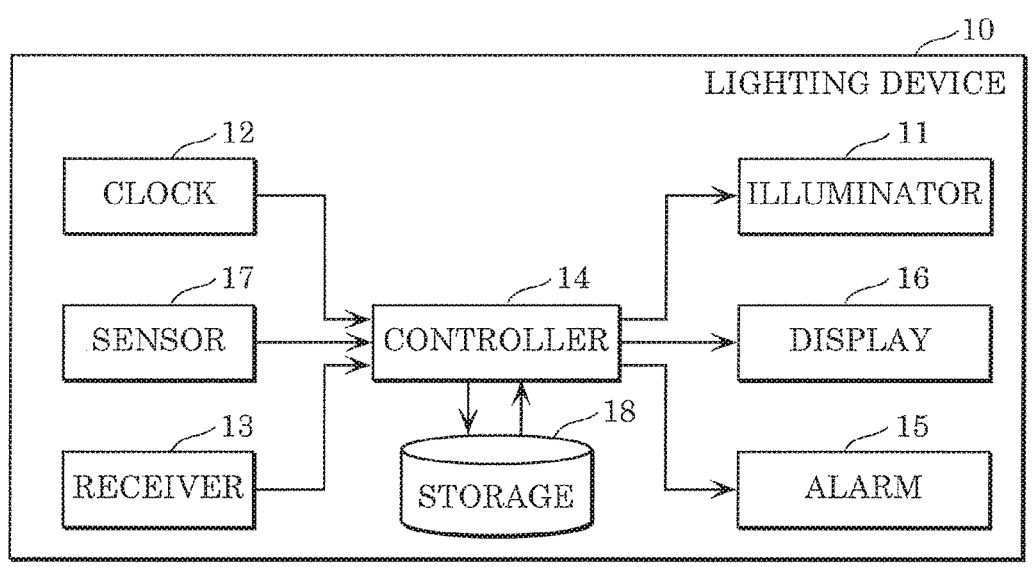
FIG. 2 is a block diagram illustrating a functional configuration of the lighting device according to Embodiment 1.

The following describes a detailed configuration of lighting device 10 according to the present embodiment with reference to FIG. 2.

FIG. 2 is a block diagram illustrating a functional configuration of lighting device 10 according to the present embodiment. As illustrated in FIG. 2, lighting device 10 includes illuminator 11, clock 12, receiver 13, controller 14, alarm 15, display 16, sensor 17, and storage 18.

Illuminator 11 emits illumination light. Specifically, illuminator 11 is a light source which emits illumination light in a visible range. For example, illuminator 11 is a light source which includes a solid-state light emitting element, and specifically, illuminator 11 includes a semiconductor light emitting element such as a light emitting diode (LED) element or a laser element, or an organic EL element, for instance. Alternatively, illuminator 11 may be a discharge lamp such as a fluorescent light.

Illuminator 11 is a light source which is at least dimmable. Specifically, controller 14 varies the output of illumination light from illuminator 11. In other words, illuminator 11 emits illumination light having the output according to a dimming level determined by controller 14. A dimming level is a proportion of illumination light relative to the maximum value (that is, the 100% dimming level) of the output of light which illuminator 11 can emit.

In the present embodiment, illuminator 11 is a light source whose color can be controlled. Specifically, controller 14 varies the correlated color temperature of illumination light from illuminator 11. In other words, illuminator 11 emits illumination light having a correlated color temperature determined by controller 14.

Clock 12 measures time. Specifically, clock 12 notifies controller 14 of a current time. Clock 12 is a clock circuit such as a so-called real-time clock, for example.

Receiver 13 receives input of a set time (at which user 1 wants to wake up) from user 1. Specifically, receiver 13 notifies controller 14 of the set time input by user 1. In the present embodiment, receiver 13 receives, from user 1, an instruction to execute wake-up control (that is, setting of an alarm). Receiver 13 may receive an instruction to stop alarm sound emitted by alarm 15. Receiver 13 notifies controller 14 of an instruction to execute wake-up control, an instruction to stop alarm sound, and others.

Receiver 13 is, for example, a button physically pressed as illustrated in FIG. 1, but is not limited to such a button. Receiver 13 may be an input interface such as a sliding switch or a touch panel.

Controller 14 performs wake-up control. Specifically, controller 14 controls illuminator 11, based on a set time. Wake-up control is control for changing the dimming level of illuminator 11, based on the set time. For example, controller 14 dims illuminator 11 by pulse width modulation (PWM) control. Wake-up control includes gradual increase control and awakening control. Controller 14 performs gradual increase control before a set time, and performs awakening control after the set time. A detailed description of wake-up control is given later.

In the present embodiment, controller 14 performs overall control of lighting device 10. Specifically, controller 14 controls outputs of illuminator 11, alarm 15, and display 16, based on information from clock 12, receiver 13, and sensor 17. Controller 14 is a program execution unit such as a processor, for example. In the present embodiment, controller 14 performs wake-up control by reading and executing a control program stored in storage 18.

In the present embodiment, controller 14 controls the dimming level of illuminator 11, in accordance with a control pattern based on a result of detection by sensor 17. Specifically, controller 14 controls the dimming level of illuminator 11, in accordance with different control patterns based on whether an eye of user 1 is open or closed. A detailed description is given later.

Alarm 15 emits alarm sound. Specifically, alarm 15 emits alarm sound at predetermined timing based on the control by controller 14. Alarm is, for example, a buzzer or a speaker included in the desk lamp (lighting device 10).

Display 16 displays predetermined control information. Predetermined control information includes a set time. Predetermined control information may also include a current time, the number of times alarm sound is produced, the number of times awakening control is performed, and others. In the present embodiment, as illustrated in FIG. 1, display 16 displays a current time and a set time. Display 16 is a liquid crystal panel or an organic electro luminescent (EL) panel, for example. Display 16 is provided at a lower portion of the desk lamp (lighting device 10) in the example illustrated in FIG. 1, but may be provided at another portion.

Sensor 17 is an example of a detector which detects a sleeping state of user 1. Specifically, sensor 17 detects whether an eye of user 1 is open. Sensor 17 is a radio wave sensor such as, for example, a millimeter wave sensor. Sensor 17 emits a radio wave toward an eye of user 1, and detects a reflected wave from the eye. The strength and the frequency, for instance, of a reflected wave differ according to whether an eye of user 1 is open or closed, and thus whether an eye of user 1 is open can be determined by analyzing the reflected wave.

Sensor 17 outputs an electrical signal according to the detected reflected wave to controller 14. Controller 14 determines, for instance, a change in the strength and the frequency of the reflected wave, based on the electrical signal output from sensor 17, and determines whether an eye of user 1 is open or closed. In other words, controller 14 determines whether user 1 has woken up.

Alternatively, sensor 17 may be an image sensor which captures an image of the face (specifically, an eye) of user 1. Sensor 17 outputs the captured image to controller 14. Controller 14 determines whether an eye of user 1 is open or closed by analyzing the image. For example, controller 14 determines whether the captured image matches a sample image showing that an eye of user 1 is open, thus determining whether an eye of user 1 is open or closed.

Storage 18 has stored programs for executing gradual increase control and awakening control which controller 14 executes. Storage 18 stores control information such as a set time input by user 1 via receiver 13. Storage 18 is a semiconductor memory such as a flash memory or a ferroelectric memory, for example.

[Wake-Up Control]

The following describes wake-up control performed by lighting device 10 according to the present embodiment, namely operation of lighting device 10, with reference to FIGS. 3 to 12B.

Note that lighting device 10 executes wake-up control if user 1 gives an instruction to execute wake-up control by operating receiver 13, for example. Alternatively, lighting device 10 may determine whether to execute wake-up control, in accordance with a predetermined schedule (which indicates that, for example, wake-up control is to be executed only on weekdays).

Figure 3:
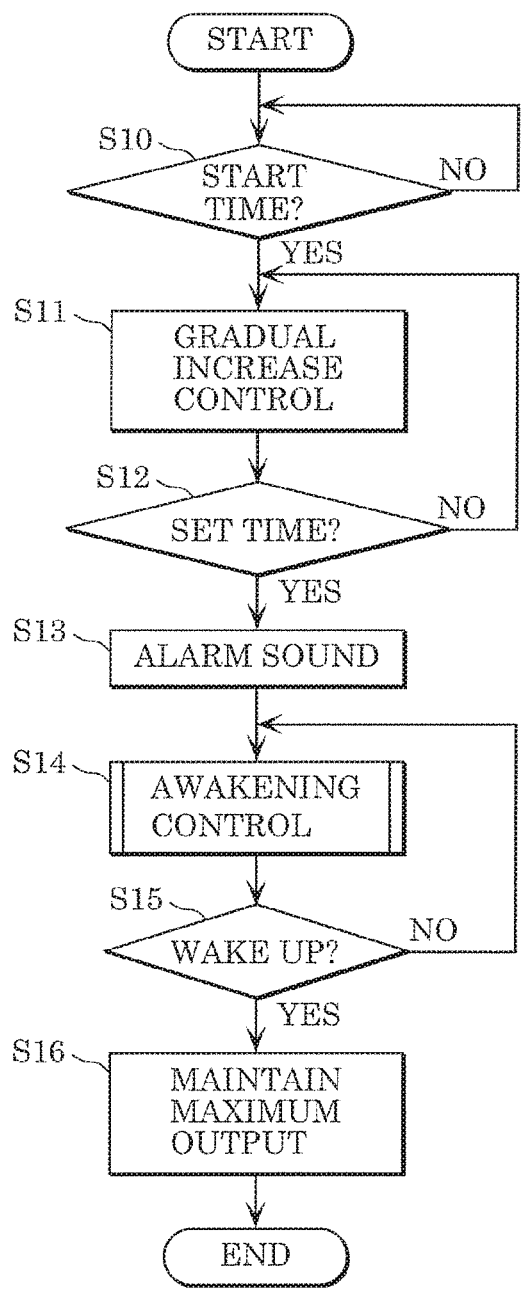
FIG. 3 is a flowchart illustrating operation of (wake-up control by) the lighting device according to Embodiment 1.
Figure 4:
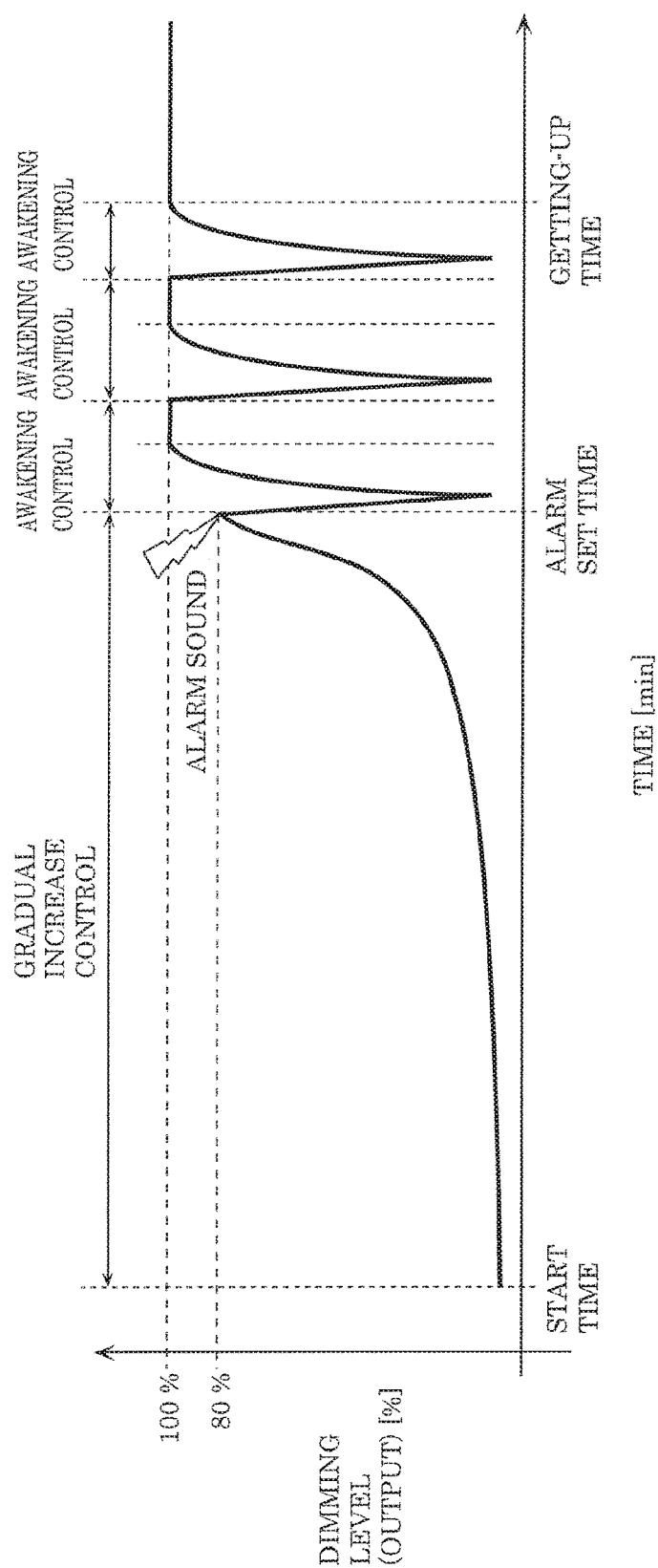
FIG. 4 illustrates a temporal change in a dimming level (light output) during wake-up control according to Embodiment 1.

FIG. 3 is a flowchart illustrating operation (wake-up control) of lighting device 10 according to the present embodiment. FIG. 4 illustrates a temporal change in the dimming level (light output) during wake-up control according to the present embodiment. Note that in FIG. 4, the horizontal axis indicates time (min: minute), and the vertical axis indicates the dimming level (%) of illuminator 11.

Note that user 1 presets a set time by operating receiver 13 in the present embodiment. For example, the set time is "7:45" in the example illustrated in FIG. 1.

As illustrated in FIG. 3, lighting device 10 is on standby until the time (current time) comes to a start time for wake-up control (NO in S10). The current time is a time notified from clock 12.

Specifically, as can be seen from FIG. 4, controller 14 maintains the dimming level of illuminator 11 at 0% before the start time. Note that the start time for wake-up control is a time prior to the set time. The start time is determined based on a time period spent for gradual increase control and the set time, for example. The time period spent for gradual increase control is, for example, at least 5 minutes and less than 150 minutes, and is 30 minutes, for example. At this time, if the set time is "7:45", the start time is "7:15" which is 30 minutes prior to the set time.

If the current time comes to the start time (YES in S10), controller 14 performs gradual increase control (S11). Gradual increase control is control for starting to emit illumination light at the start time and gradually increasing the dimming level until the set time. Controller 14 causes illuminator 11 to emit illumination light having a predetermined low dimming level at the start time by controlling illuminator 11, as illustrated in FIG. 4. The dimming level at the start time is, for example, a minimum value (for example, 5%) of a range in which illuminator 11 can emit illumination light.

Note that the gradual increase control is divided into a first half and a latter half. In the first half, the dimming level is lower and changes less than the dimming level in the latter half. For example, the first half is a period in which the amount of change in dimming level per unit time is maintained constant, and the latter half is a period in which the amount of change in dimming level per unit time is gradually increased. The first half lasts longer than the latter half. In the present embodiment, the slope of the temporal change in the dimming level is zero or more throughout the gradual increase control. Accordingly, gradual increase control according to the present embodiment does not decrease the dimming level. In this manner, by gradual increase control, the dimming level of illuminator 11 increases slowly and little by little (in the first half), and rapidly increases as the current time comes near the set time (in the latter half).

When the current time comes to the set time (YES in S12), controller 14 causes alarm 15 to emit alarm sound by controlling alarm 15 (S13). Specifically, alarm 15 produces alarm sound under the control of controller 14 during a predetermined period (hereinafter, referred to as an "alarm period"). During the alarm period, if receiver 13 receives stoppage of alarm sound from user 1, controller 14 stops alarm 15 producing the alarm sound, and starts awakening control. If receiver 13 does not receive stoppage of the alarm sound from user 1, after the alarm period has elapsed, controller 14 stops alarm 15 producing the alarm sound, and starts awakening control.

Controller 14 performs awakening control, after alarm sound is produced (S14). The following describes details of awakening control (S14) with reference to FIGS. 5 and 6.

Figure 5:
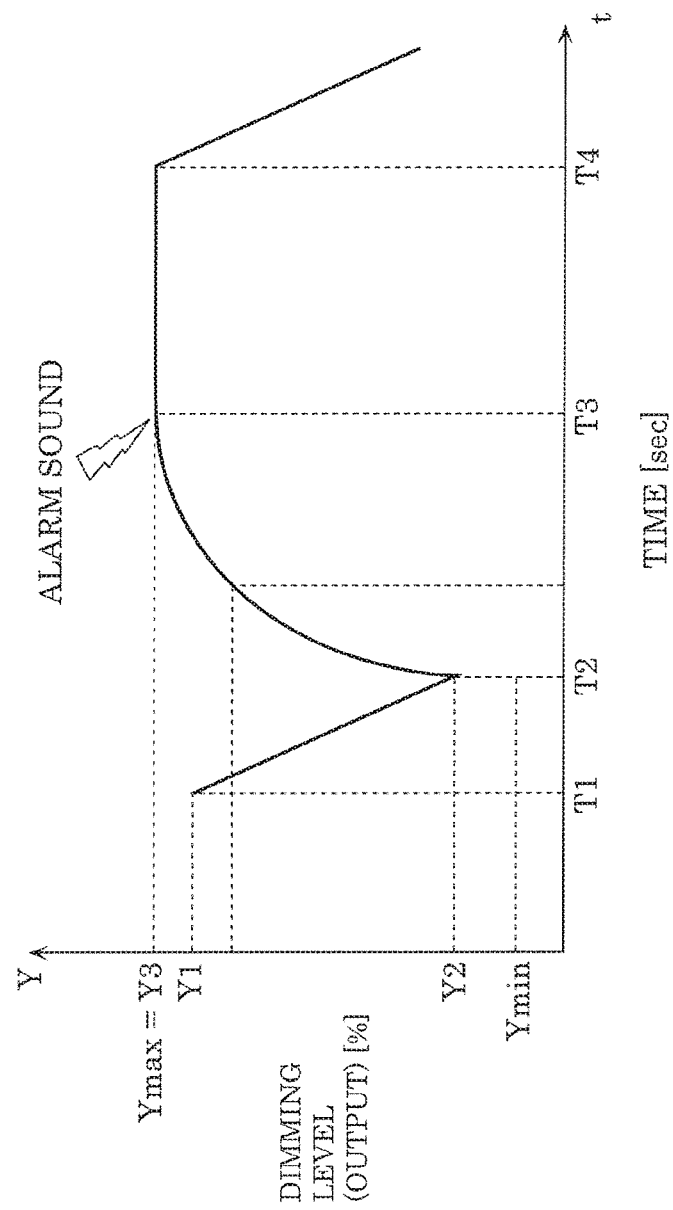
FIG. 5 illustrates a temporal change in the dimming level during awakening control according to Embodiment 1.
Figure 6:
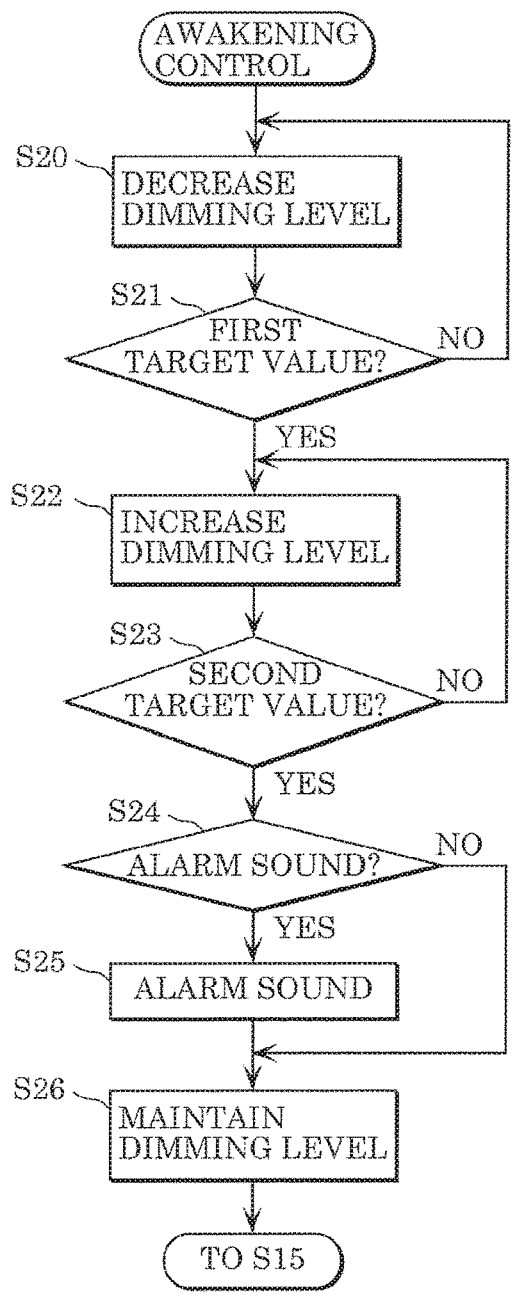
FIG. 6 is a flowchart illustrating awakening control by the lighting device according to Embodiment 1.

FIG. 5 illustrates a temporal change in the dimming level during awakening control of lighting device 10 according to the present embodiment. FIG. 6 is a flowchart illustrating awakening control of lighting device 10 according to the present embodiment. In FIG. 5, the horizontal axis represents time (sec: second), and the vertical axis represents the dimming level (%) of illuminator 11.

As illustrated in FIG. 6, controller 14 first decreases the dimming level (S20). Controller 14 decreases the dimming level until the dimming level reaches a first target value (No in S21).

Specifically, controller 14 decreases the dimming level of illuminator 11 over a period from first time T1 at or after the set time to second time T2, as illustrated in FIG. 5. First time T1 is a time when user 1 has stopped alarm sound or a time when the alarm period has elapsed without user 1 stopping alarm sound. Second time T2 is a time when the dimming level has reached the first target value which is a predetermined target value.

In the example illustrated in FIG. 5, controller 14 decreases the dimming level of illuminator 11 from dimming level Y1 at first time T1 down to dimming level Y2 which is the first target value. Dimming level Y1 is a value lower than a maximum value of the output of light which illuminator 11 can emit, namely, maximum value Ymax of the dimming level (specifically, 100%), but is not limited to such a value. Dimming level Y1 may have maximum value Ymax.

Note that as illustrated in FIG. 4, dimming level Y1 is a dimming level at the set time which is, for example, 80% in a first iteration of awakening control. In contrast, in a second iteration of awakening control, dimming level Y1 is a dimming level at a point in time (fourth time T4) when previous awakening control has ended, and is 100%, for example. In this manner, dimming level Y1 may have different values in iterations of awakening control.

In the present embodiment, dimming level Y2 is 26% or less. Substantially the same state as a dark state (0% dimming level) can be created for user 1 whose eyes are closed, by setting dimming level T2 at second time T2 to 26% or less. In the example illustrated in FIG. 5, dimming level Y2 is a value higher than a minimum value of the output of light which illuminator 11 can emit, or in other words, minimum value Ymin of the dimming level, but is not limited to such a value. Dimming level Y2 may be minimum value Ymin. Minimum value Ymin is 5%, for example.

In the present embodiment, controller 14 decreases, at a constant rate, the dimming level from dimming level Y1 to dimming level Y2, for example. Alternatively, controller 14 may vary the rate of decrease.

If the dimming level reaches the first target value (YES in S21), controller 14 increases the dimming level (S22). Controller 14 increases the dimming level until the dimming level reaches a second target value (NO in S23).

Specifically, controller 14 increases the dimming level of illuminator 11 over a period from second time T2 to third time T3, as illustrated in FIG. 5. Third time T3 is a time when the dimming level has reached the second target value which is a predetermined target value.

In the example illustrated in FIG. 5, controller 14 increases the dimming level of illuminator 11 from dimming level Y2 at second time T2 up to dimming level Y3 which is the second target value. Dimming level Y3 is dimming level Ymax in the present embodiment, but is not limited to this value. Dimming level Y3 may be equal to dimming level Y1, for example, or may be greater or smaller than dimming level Y1.

Figure 7:
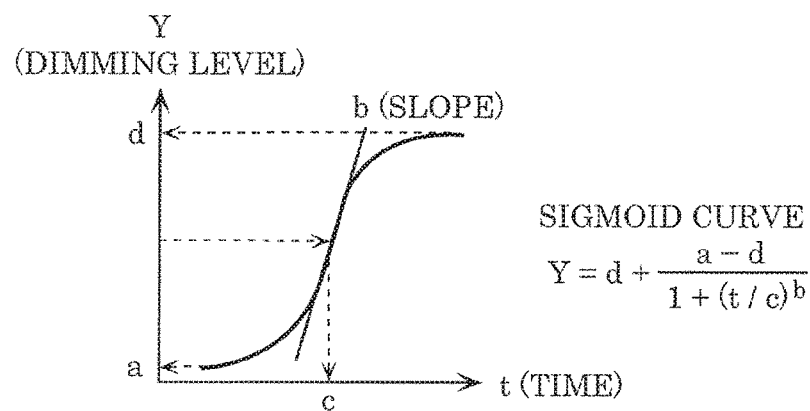
FIG. 7 illustrates a sigmoid curve.

In the present embodiment, controller 14 increases the dimming level over a period from second time T2 to third time T3, based on predetermined conditions. For example, controller 14 temporally increases the dimming level, based on a predetermined function. Constants of the predetermined function have features at this time. Specifically, in the awakening control, controller 14 controls the dimming level from second time T2 to third time T3, based on a function expressed by, using constants a, b, c, and d:

[Math 1]

$$Y = d + \frac{a-d}{1+(t/c)^b} \quad (1)$$

where Y denotes the dimming level and t denotes time. At this time, constant c is a value closer to second time T2 than third time T3. Note that function (1) is a so-called sigmoid function (sigmoid curve). FIG. 7 illustrates a sigmoid curve.

As illustrated in FIG. 7, constant a is the minimum value of the dimming level, and constant d is the maximum value of the dimming level. Constant c is a point of inflection of the sigmoid curve, and specifically is a time when the slope is the greatest. Constant b is a slope at the point of inflection (constant c).

Figure 8:
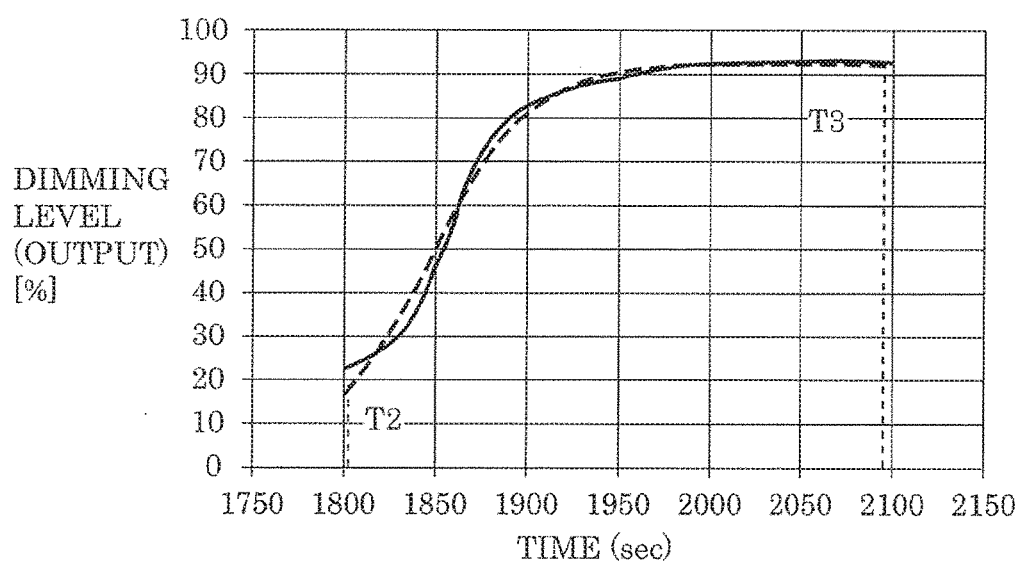
FIG. 8 illustrates an example in which a temporal change in the dimming level is fitted to a sigmoid curve.

In the present embodiment, controller 14 controls the dimming level according to a sigmoid function with which constant c is a value closer to second time T2 than third time T3. Alternatively, controller 14 may control the dimming level in accordance with any function such as an n-th function including a concave-down quadratic function, an exponential function, or a logarithmic function, rather than the sigmoid function. In this case, if a temporal change in the dimming level based on an actually measured value of illuminance of light emitted by illuminator 11 is fitted to function (1) above, constant c may consequentially become a value closer to second time T2 than third time T3, as illustrated in FIG. 8.

Fitting is performed based on the least square method, for example. FIG. 8 illustrates an example in which a temporal change in the dimming level based on an actually measured value of the illuminance is fitted to the sigmoid curve. The thick line indicates an actual change in the dimming level, and the thick dashed line indicates a result of fitting the actual change to function (1).

Specifically, constants (specifically, a, b, c, and d) which minimize a sum total of the square of residuals between a target curve (specifically, a pattern for controlling the dimming level based on an actually measured value) and a regression curve (specifically, function (1)) is determined by changing numerical values of the constants of the regression curve with respect to the target curve.

In the present embodiment, controller 14 further controls the correlated color temperature of illumination light from second time T2 to third time T3. Specifically, controller 14 controls the correlated color temperature according to the dimming level of illumination light.

Figure 9:
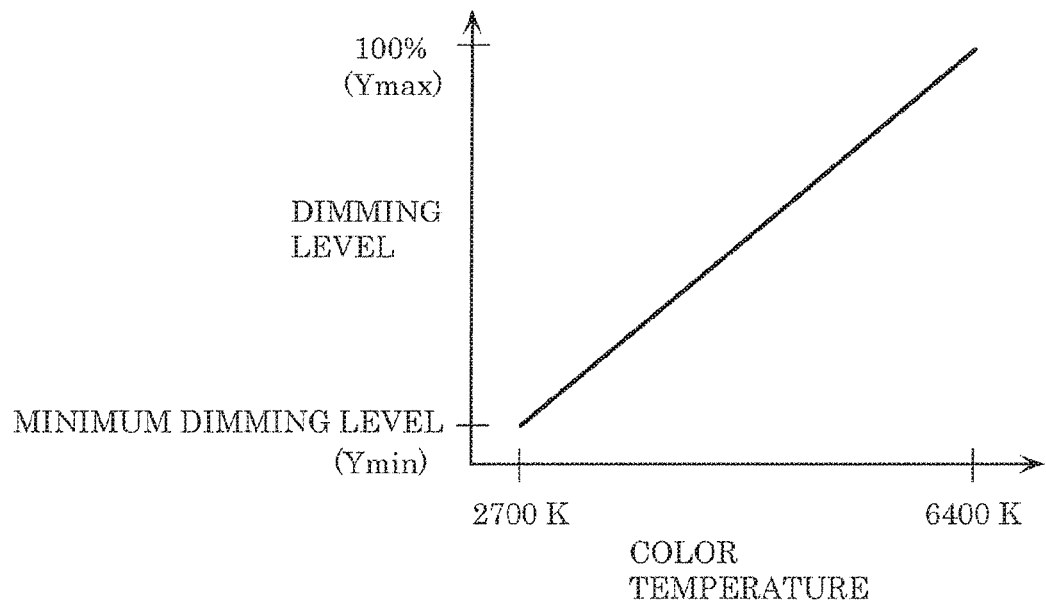
FIG. 9 illustrates a relation between a correlated color temperature and the dimming level of an illuminator of the lighting device according to Embodiment 1.

FIG. 9 illustrates the relation between a correlated color temperature and the dimming level of illuminator 11 of lighting device 10 according to the present embodiment. In FIG. 9, the horizontal axis represents the correlated color temperature of illuminator 11, and the vertical axis represents the dimming level.

For example, controller 14 controls the correlated color temperature based on the dimming level of illumination light, to satisfy the relation illustrated in FIG. 9. Specifically, the relation between the dimming level and the correlated color temperature in a period from second time T2 to third time T3 has a substantially linear form. The correlated color temperature ranges, for example, from electric lamp color (2700K) to daylight color (6400K), but the range is not limited to this.

Referring back to FIG. 6, if the dimming level reaches the second target value (YES in S23), and if it is determined that alarm sound is to be produced (YES in S24), controller 14 causes alarm 15 to emit alarm sound by controlling alarm 15 (S25). In other words, controller 14 causes alarm 15 to emit alarm sound at third time T3.

Figure 10A:
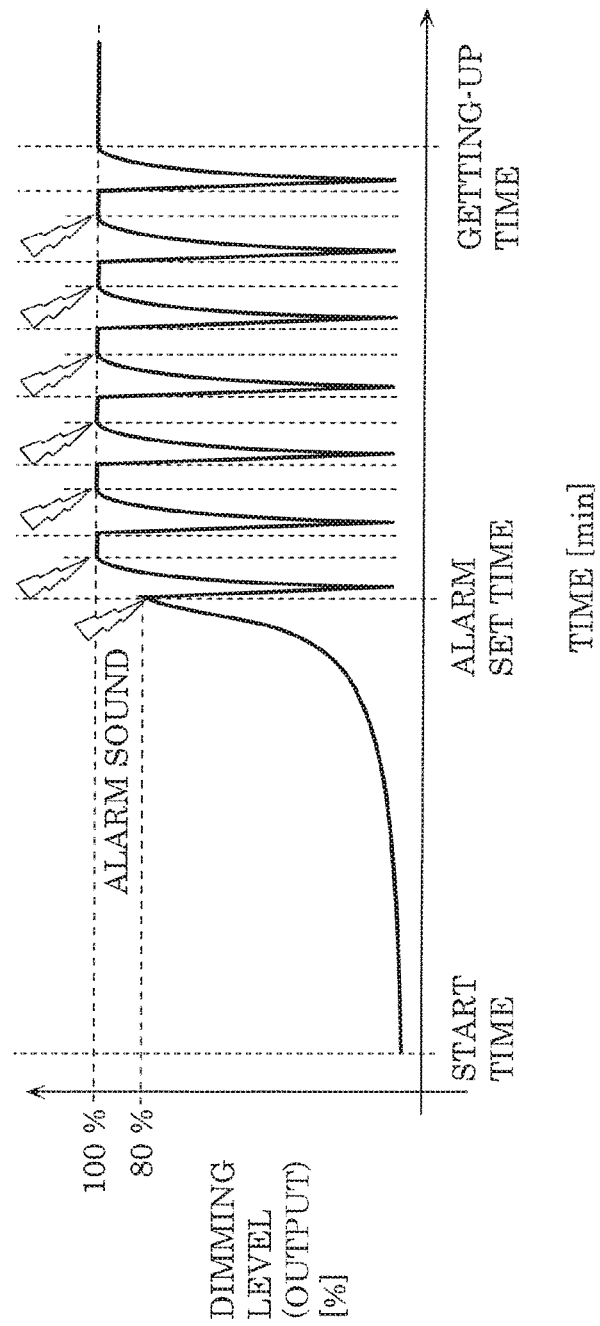
FIG. 10A is an explanatory diagram illustrating operation of an alarm of the lighting device according to Embodiment 1.
Figure 10B:
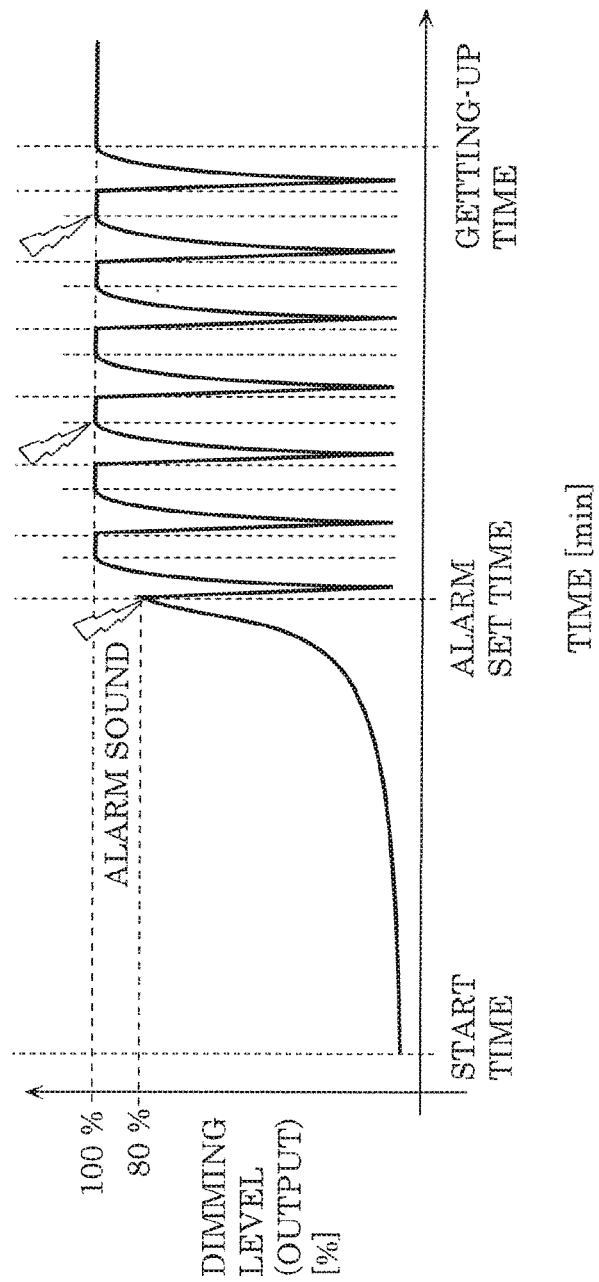
FIG. 10B is an explanatory diagram illustrating another example of operation of the alarm of the lighting device according to Embodiment 1.

Controller 14 determines whether alarm 15 is to produce alarm sound, based on predetermined conditions. FIGS. 10A and 10B are drawings for illustrating operation of alarm 15 of lighting device 10 according to the present embodiment.

For example, as illustrated in FIG. 10A, controller 14 may cause alarm 15 to emit alarm sound at third time T3 in each iteration of awakening control. Alternatively, as illustrated in FIG. 10B, controller 14 may intermittently cause alarm 15 to emit alarm sound at third time T3 in iterations of awakening control. Specifically, controller 14 may cause alarm 15 to emit alarm sound once in N iterations (N is a natural number). In the example illustrated in FIG. 10B, controller 14 may cause alarm 15 to emit alarm sound once in three iterations.

After alarm sound is emitted, controller 14 maintains the dimming level of illuminator 11 for a predetermined period (S26). Specifically, controller 14 maintains the dimming level at third time T3, from third time T3 to fourth time T4, as illustrated in FIG. 5. Note that a period during which controller 14 maintains the dimming level may be predetermined, or may end when user 1 stops alarm sound.

In awakening control, a period which lasts to decrease the dimming level, or in other words, a period from first time T1 to second time T2 is not particularly limited, but may be 2 seconds, for example. A period which lasts to increase the dimming level, or in other words, a period from second time T2 to third time T3 is not particularly limited, but may be 8 seconds, for example. A period during which the dimming level is maintained, or in other words, a period from third time T3 to fourth time T4 is not particularly limited, but may be 50 seconds, for example.

In the present embodiment, a period from first time T1 to third time T3 is shorter than a period from the start time to the set time, namely a period for gradual increase control. Specifically, a period from first time T1 to fourth time T4, namely a period for one awakening control, is shorter than the period for gradual increase control. For example, a period from first time T1 to third time T3 lasts 1 minute or less. A period from first time T1 to fourth time T4 may be 1 minute or less.

When the current time comes to fourth time T4, the processing proceeds to step S15 illustrated in FIG. 3, where controller 14 determines whether user 1 has woken up.

Controller 14 iterates awakening control (S14) until user 1 wakes up (NO in S15). Specifically, controller 14 determines whether user 1 has woken up based on notification from sensor 17. If user 1 has not woken up, controller 14 iterates awakening control.

Figure 11:
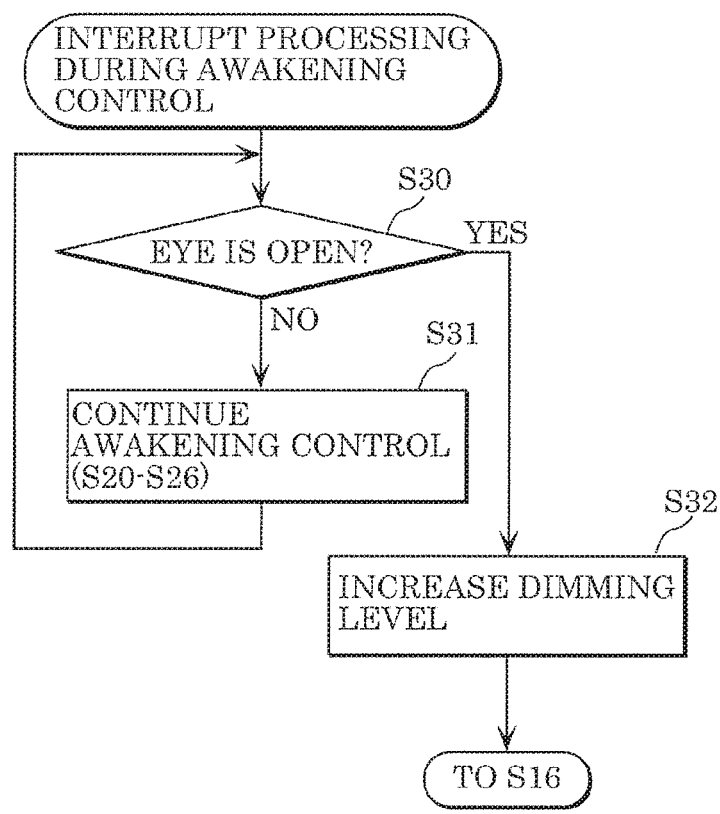
FIG. 11 is a flowchart illustrating interrupt processing by the lighting device according to Embodiment 1 during awakening control.

In the present embodiment, whether user 1 has woken up is determined based on a result of detection by sensor 17 whether an eye of user 1 is open or closed. Specifically, controller 14 executes, based on the detection result, determination as to whether a user has woken up as interrupt processing during awakening control. FIG. 11 is a flowchart illustrating interrupt processing during awakening control according to the present embodiment.

Controller 14 determines whether an eye of user 1 is open or closed (S30). If controller 14 determines that an eye of user 1 is not open, in other words, is closed (NO in S30), controller 14 continues awakening control. Specifically, controller 14 performs a step of the awakening control illustrated in FIG. 6, which has been performed (S31). If controller 14 determines that an eye of user 1 is open (YES in S30), controller 14 increases the dimming level of illuminator 11 to the maximum value (S32).

After that, the processing proceeds to step S16 illustrated in FIG. 3, where controller 14 maintains the dimming level at the maximum value. Note that the getting-up time in FIG. 4 indicates the time when user 1 gets up. Controller 14 maintains the dimming level at a predetermined value (for example, the maximum value) after the getting-up time.

Figure 12A:
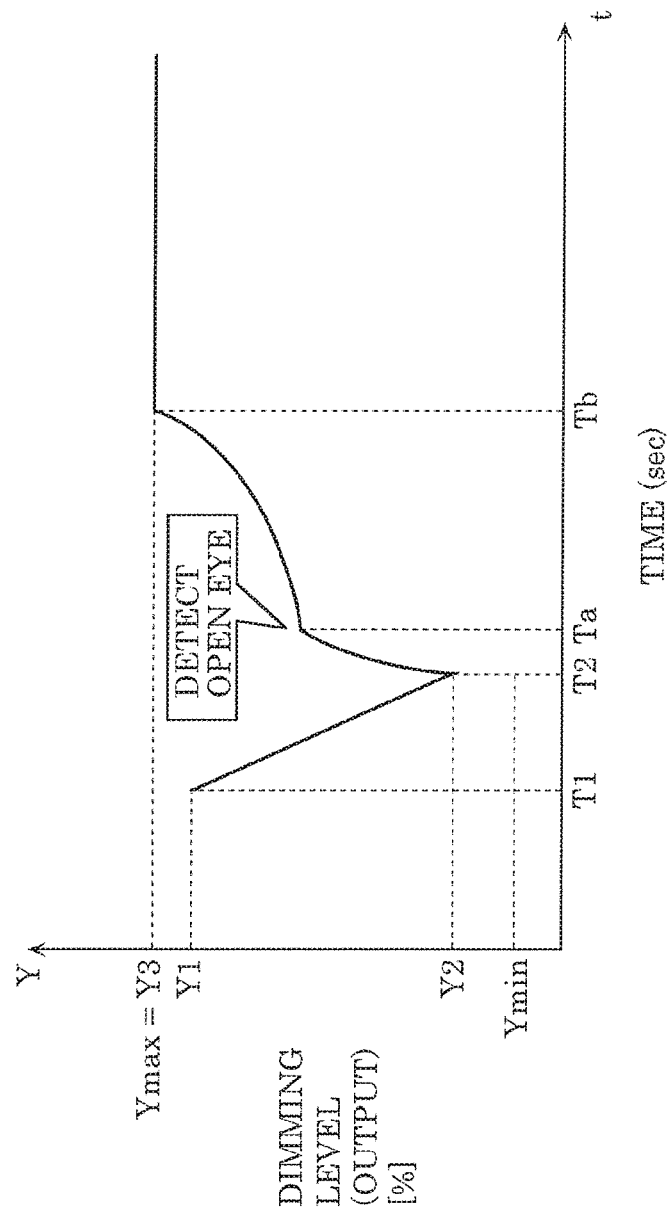
FIG. 12A illustrates a temporal change in the dimming level when an open eye is detected during awakening control according to Embodiment 1.

FIG. 12A illustrates a temporal change in the dimming level when an open eye is detected during awakening control according to the present embodiment. In FIG. 12A, the horizontal axis represents time (sec: second), and the vertical axis represents the dimming level (%) of illuminator 11. FIG. 12A illustrates the case where sensor 17 detects that an eye of user 1 is open while the dimming level is increased over a period from second time T2 to third time T3.

As illustrated in FIG. 12A, controller 14 performs open-eye control upon detecting that an eye of user 1 is open. Specifically, controller 14 increases the dimming level on a condition (in accordance with a control pattern) different from that for when an eye of user 1 is open. As a result, if a temporal change in the dimming level from time Ta which is a time when open-eye control starts until time Tb when the dimming level reaches the maximum value is fitted to function (1) above, constant c becomes a value close to time Tb.

For example, if controller 14 determines that an eye of user 1 is open, controller 14 controls the dimming level in accordance with a sigmoid function with which constant c is a value closer to time Tb than time Ta. Alternatively, controller 14 may control the dimming level in accordance with any function such as an n-th function including a concave-up quadratic function, an exponential function, and a logarithmic function, rather than a sigmoid function. If a temporal change in the dimming level is fitted to function (1) above, constant c may become a value closer to time Tb than time Ta, as illustrated in FIG. 12A.

Controller 14 maintains the dimming level at the maximum value after the dimming level has reached the maximum value. Accordingly, controller 14 maintains the dimming level of illuminator 11 at the maximum value if sensor 17 detects that an eye of user 1 is open.

Figure 12B:
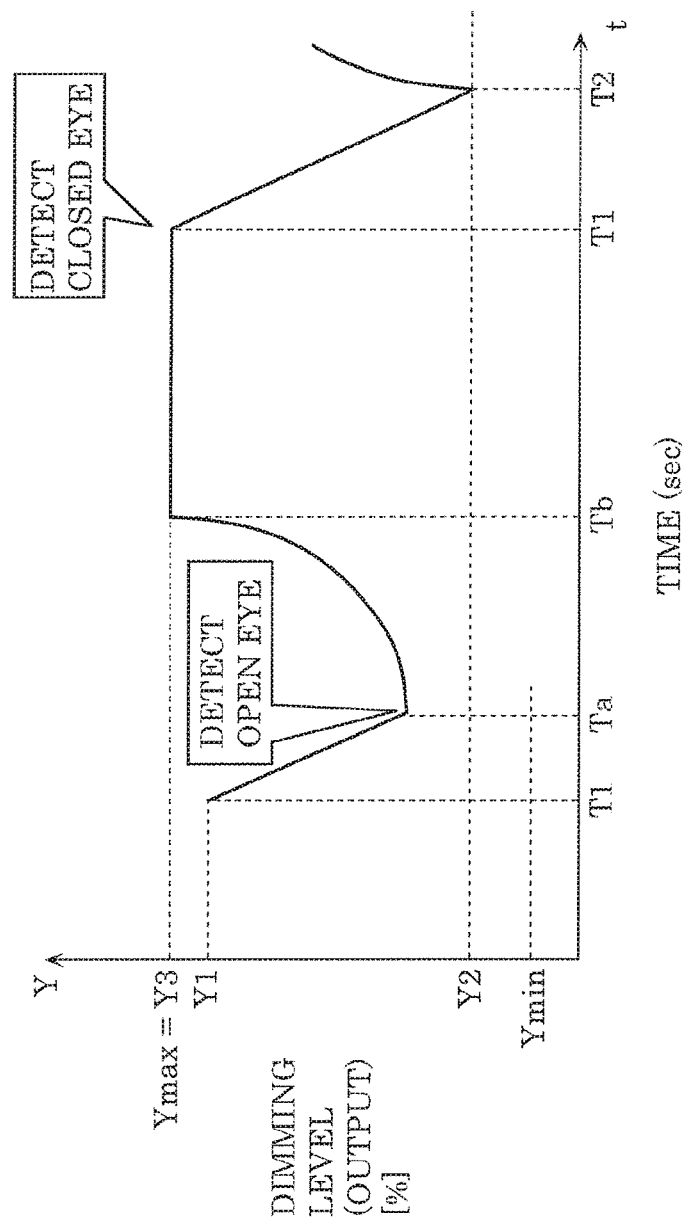
FIG. 12B illustrates a temporal change in the dimming level when a closed eye is detected again after an open eye is detected in Embodiment 1.

Furthermore, the same also applies to the case where sensor 17 detects that an eye of user 1 is open while the dimming level is decreased over a period from first time T1 to second time T2, as illustrated in FIG. 12B. Note that controller 14 maintains the dimming level at the maximum value as it is, if sensor 17 detects that an eye of user 1 is open during a period from third time T3 to fourth time T4 in which the dimming level is maintained at the maximum value.

Note that it is possible to assume that an eye of user 1 is once determined to be open, but is closed again and thus determined to be closed. In other words, it is possible to assume that user 1 goes back to sleep. FIG. 12B illustrates a temporal change made when an open eye is detected and thereafter a closed eye is detected again, in the present embodiment. In FIG. 12B, a closed eye is detected during a period in which the dimming level is maintained at the maximum value since an open eye has been detected.

As illustrated in FIG. 12B, controller 14 performs awakening control, if sensor 17 detects that an eye of user 1 is closed. In other words, controller 14 starts awakening control at first time T1 which is a time when sensor 17 detects that an eye of user 1 is closed. Controller 14 thereafter iterates awakening control if sensor 17 does not detect that an eye of user 1 is open.

Note that the present embodiment has described an example in which as interrupt processing, an eye is detected and determined to be open or closed at all times, but is not limited to this example. Controller 14 may detect whether an eye is open or closed at predetermined timing. For example, controller 14 may determine whether an eye is open or closed at a time when first awakening control has ended, or specifically, fourth time T4 (or third time T3).

[Results of Experiments on Wake-Up Control]

Here, a description of results of experiments on actually waking up user 1 by lighting device 10 according to the present embodiment, with reference to FIG. 13A. FIG. 13A illustrates results of experiments on wake-up control according to the present embodiment.

Specifically, an experiment based on the embodiment which includes both gradual increase control and awakening control and an experiment based on a comparative example which includes only gradual increase control are conducted on subjects, and the subjects subjectively evaluated how the subjects felt when the subjects woke up. Ten men and women aged from twenties to fifties were selected as the subjects. Experiments on the embodiment and the comparative example were conducted one week each.

Five semantic differential (SD) evaluation indexes were used for items of subjective evaluation made when the subjects woke up. Feeling and sleepiness of the subjects when the subjects woke up were evaluated on a five-level scale, namely, "+2" to "−2". For the feeling of the subjects at wake-up time, "+2" represents "feel very good" and "−2" represents "feel very bad". Similarly, also for the sleepiness of the subjects at wake-up time, "+2" represents "not sleepy at all" and "−2" represents "very sleepy".

As illustrated in FIG. 13A, both feeling and sleepiness of the subjects at wake-up time show better evaluations when gradual increase control and awakening control were performed than when only gradual increase control was performed. Accordingly, lighting device 10 according to the present embodiment achieves making user 1 feel good and also less sleepy at wake-up time. Lighting device 10 thus pleasantly wakes up user 1.

In awakening control, a greater amount of illumination light emitted to user 1 and a greater change in the amount of the illumination light result better to pleasantly wake up user 1. Accordingly, for example, dimming level Y2 at second time T2 which is a minimal value of the dimming level in awakening control may be the greatest possible value and furthermore a value which makes user 1 feel a considerable change in the amount of light. In view of this, the following experiments were conducted in order to obtain an appropriate value of dimming level Y2.

Specifically, experiments were conducted on subjects, nine men and women aged from twenties to sixties, using a typical ceiling lighting device. When a control condition is that the output of a lighting device is minimum, each subject was alternately under the control condition and an experimental condition for 5 seconds each from a light-adapted state, and thereafter the subject answered whether it was dark under the condition. The subjects were lying on his/her back with the eyes closed all the time, specifically, when the eyes were adapting to light, when the subjects were placed under a condition, and when the subject evaluated the condition.

Seven conditions and a control stimulus were randomly presented so that the order of presenting the seven conditions and the order of presenting the seven conditions and the control stimulus (two sequential levels) do not show the order effect. Each subject made ten evaluations for each condition.

Logistic regression analysis is conducted, for each subject, on percentages of the subject saying it was dark under the conditions, to calculate a threshold of the subject. As a result, the $R^2$ value of a regression curve indicates a high value (>0.7), thus showing that the regression is appropriate. As a result of calculating the average of thresholds (threshold of 75%) of the subjects, the result obtained was 26%, as illustrated in FIG. 13B. Note that FIG. 13B illustrates results of experiments for obtaining an appropriate value of dimming level Y2 at second time T2 according to the present embodiment. The horizontal axis indicates identification numbers (IDs) of the subjects, and the vertical axis indicates an average of output levels, at which a subject perceives that it is bright, relative to a bright state.

If the environment having certain brightness is changed to a dark environment while the eyes of a subject are closed, and if the output is 26% of the output for the original brightness, the subject perceives substantially the same brightness as when the output is less than 26% of the original output. In other words, this means that a subject perceives that a change in the light amount made when the output is changed from 26% or less is substantially the same as a change in the light amount made when the output is changed from 0%.

Accordingly, for example, if dimming level Y2 at second time T2 is 26%, the amount of illumination light to be emitted to user 1 can be increased while the amount of light is changed to the greatest extent. Accordingly, user 1 can be pleasantly woken up.

Advantageous Effects and Others

As described above, lighting device 10 according to the present embodiment includes: illuminator 11 which emits illumination light; clock 12 which measures time; receiver 13 which receives input of a set time from user 1; sensor 17 which detects whether an eye of user 1 is open; controller 14 which controls, at or after the set time, a dimming level of illuminator 11, in accordance with a control pattern based on a result of the detection by sensor 17.

In this manner, at or after the set time, the dimming level is changed according to whether an eye of user 1 is open or closed, and thus dimming control according to the awakened level of user 1 can be performed. Accordingly, user 1 can be awakened quickly, while reducing discomfort which user 1 feels. User 1 can be thus pleasantly woken up.

For example, when sensor 17 does not detect that an eye of user 1 is open, controller 14 performs awakening control for decreasing the dimming level of illuminator 11 over a period from first time T1 at or after the set time to second time T2 and increasing the dimming level over a period from second time T2 to third time T3, and in the awakening control, controller 14 controls the diming level from second time T2 to third time T3, based on function (1) expressed, using constants a, b, c, and d, where Y denotes the dimming level and t denotes time, and constant c is a value closer to second time T2 than third time T3.

In this manner, while reducing unpleasant stimuli due to a rapid change in the amount of light, a change in the amount of light can be presented to user 1, and thus user 1 can be pleasantly woken up. For example, an improvement in the feeling of user 1 and a reduction in sleepiness of user 1 when user 1 wakes up can be both achieved as illustrated in FIG. 13A. Accordingly, lighting device 10 according to the present embodiment can pleasantly wake up user 1.

For example, controller 14 controls the dimming level of illuminator 11 at the maximum value after sensor 17 detects that an eye of user 1 is open.

This allows a great amount of light to be emitted to user 1 whose eye is open. Accordingly, user 1 can be pleasantly woken up.

For example, controller 14 performs open-eye control for increasing the dimming level to the maximum value when sensor 17 detects that an eye of user 1 is open, and controller 14 controls the diming level in the open-eye control, based on function (1), and constant c of function (1) during the open-eye control is a value closer to time Tb when a dimming level reaches the maximum value than start time Ta of the open-eye control.

In this manner, when an eye of user 1 is open, the dimming level can be increased gradually, and thus user 1 can be awakened quickly, while reducing discomfort which user 1 feels.

For example, controller 14 iterates the awakening control when sensor 17 does not detect that an eye of user 1 is open.

In this manner, iteration of awakening control promotes awakening user 1.

For example, during the awakening control, controller 14 further maintains a dimming level at third time T3, from third time T3 to fourth time T4.

This extends a period in which user 1 is exposed to a great amount of light, and thus user 1 can be pleasantly woken up.

For example, alarm 15 which emits alarm sound is further included, and during the awakening control, controller 14 further causes alarm 15 to emit the alarm sound at third time T3.

This gives user 1 not only a light stimulus, but also a sound stimulus, and thus awakening of user 1 can be strongly promoted.

For example, in iteration of the awakening control, controller 14 intermittently causes alarm 15 to emit the alarm sound at third time T3.

This prevents alarm sound from being emitted in each time awakening control is iterated, and thus inconvenience that alarm sound is emitted in each iteration can be reduced.

For example, controller 14 further performs gradual increase control for causing illuminator 11 to start emitting the illumination light at a start time prior to the set time, and gradually increasing the dimming level until the set time.

In this manner, gradual increase control can make user 1 sleep light, and thus subsequent awakening control can more strongly promote awakening user 1. Furthermore, user 1 wakes up while user 1 is sleeping light, and thus feeling of user 1 when user 1 wakes up can be improved, and also sleepiness of user 1 when user 1 wakes up can be reduced.

Figure 14:
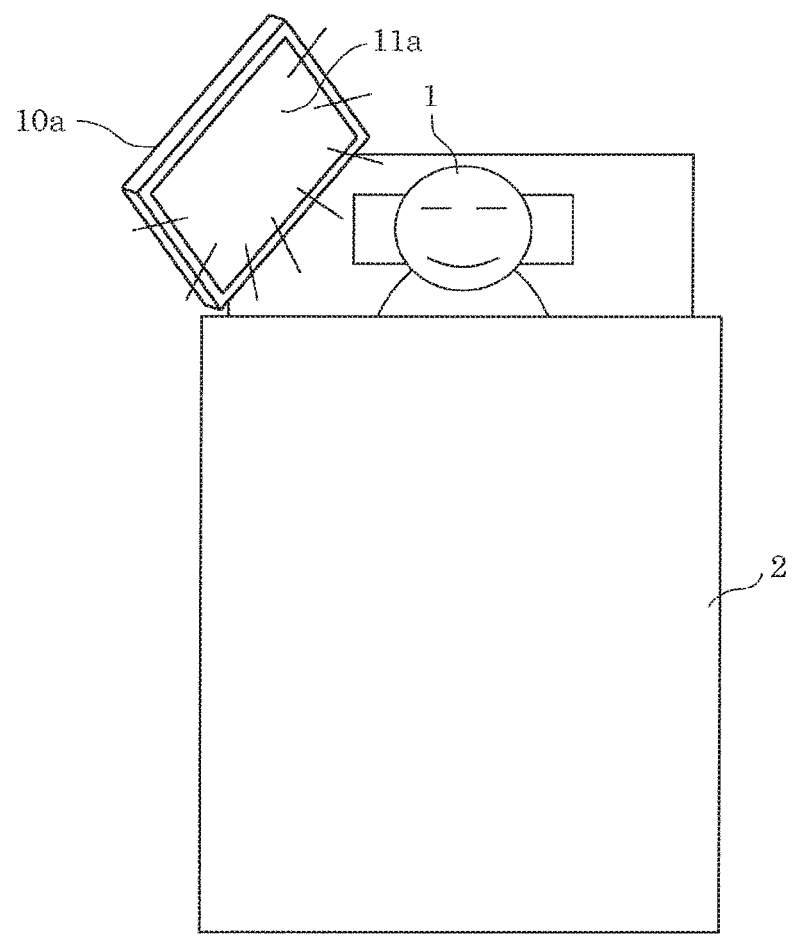
FIG. 14 is a schematic diagram illustrating a lighting device according to a variation of Embodiment 1 and a use environment of the lighting device.

Note that the present embodiment has described an example in which lighting device 10 is a desk-lamp lighting device, yet lighting device 10 is not limited to such a device. FIG. 14 is a schematic diagram illustrating lighting device 10a according to a variation of the present embodiment and a use environment of lighting device 10a.

Lighting device 10a according to this variation is a tablet terminal. Lighting device 10a includes touch panel display 11a. Touch panel display 11a achieves functions of illuminator 11, receiver 13, and display 16 according to the present embodiment.

Note that lighting device 10a may be a personal digital assistant such as a smartphone or a display device such as a TV or a monitor of a personal computer, rather than a tablet terminal.

Embodiment 2

The following describes a lighting system according to Embodiment 2. In Embodiment 1 above, lighting device 10 independently performs wake-up control, whereas in a lighting system according to the present embodiment, a plurality of devices cooperatively perform wake-up control. Note that in the following description, the same numeral is given to the same element as that of Embodiment 1, and a description thereof is omitted or simplified.

Figure 15:
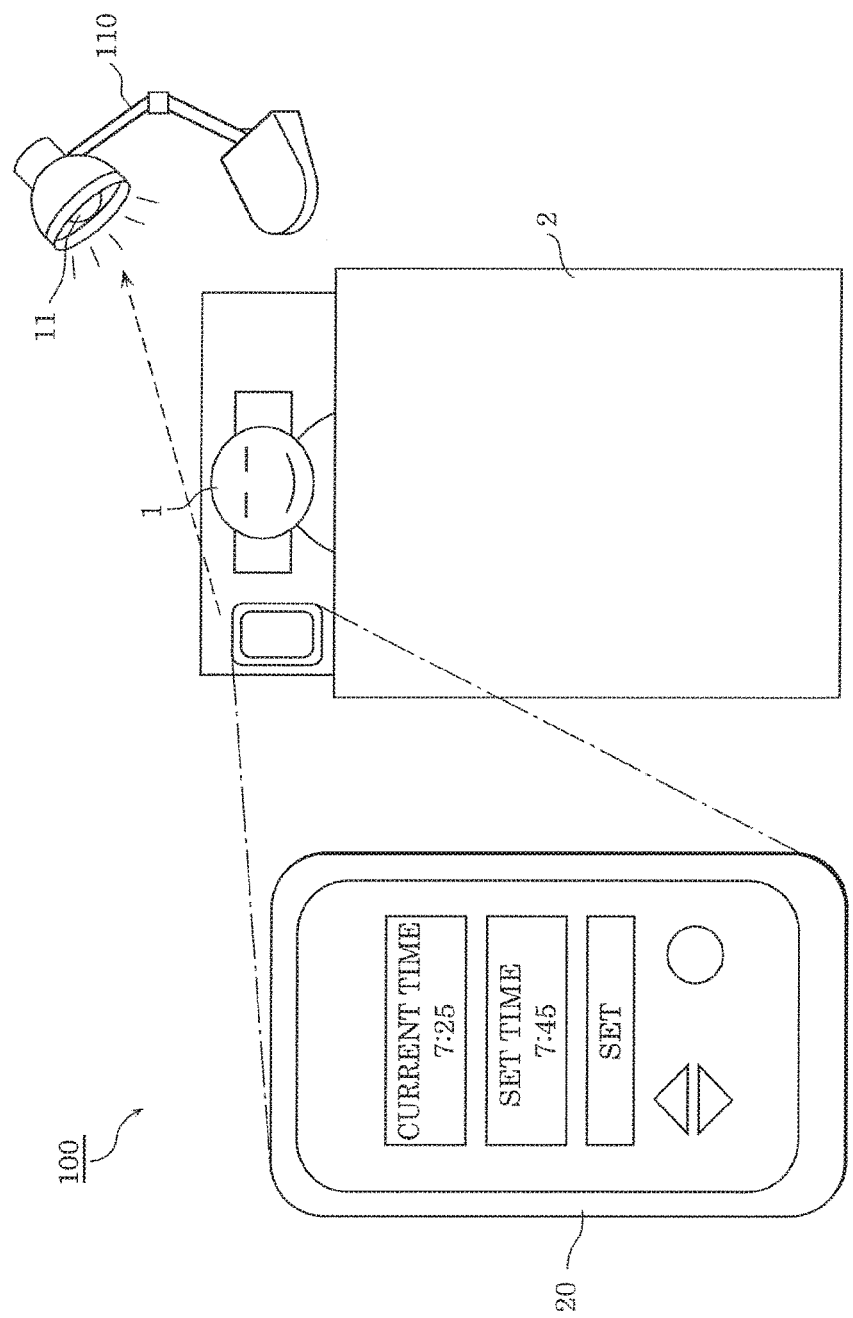
FIG. 15 is a schematic diagram illustrating a lighting system according to Embodiment 2 and a use environment of the lighting system.
Figure 16:
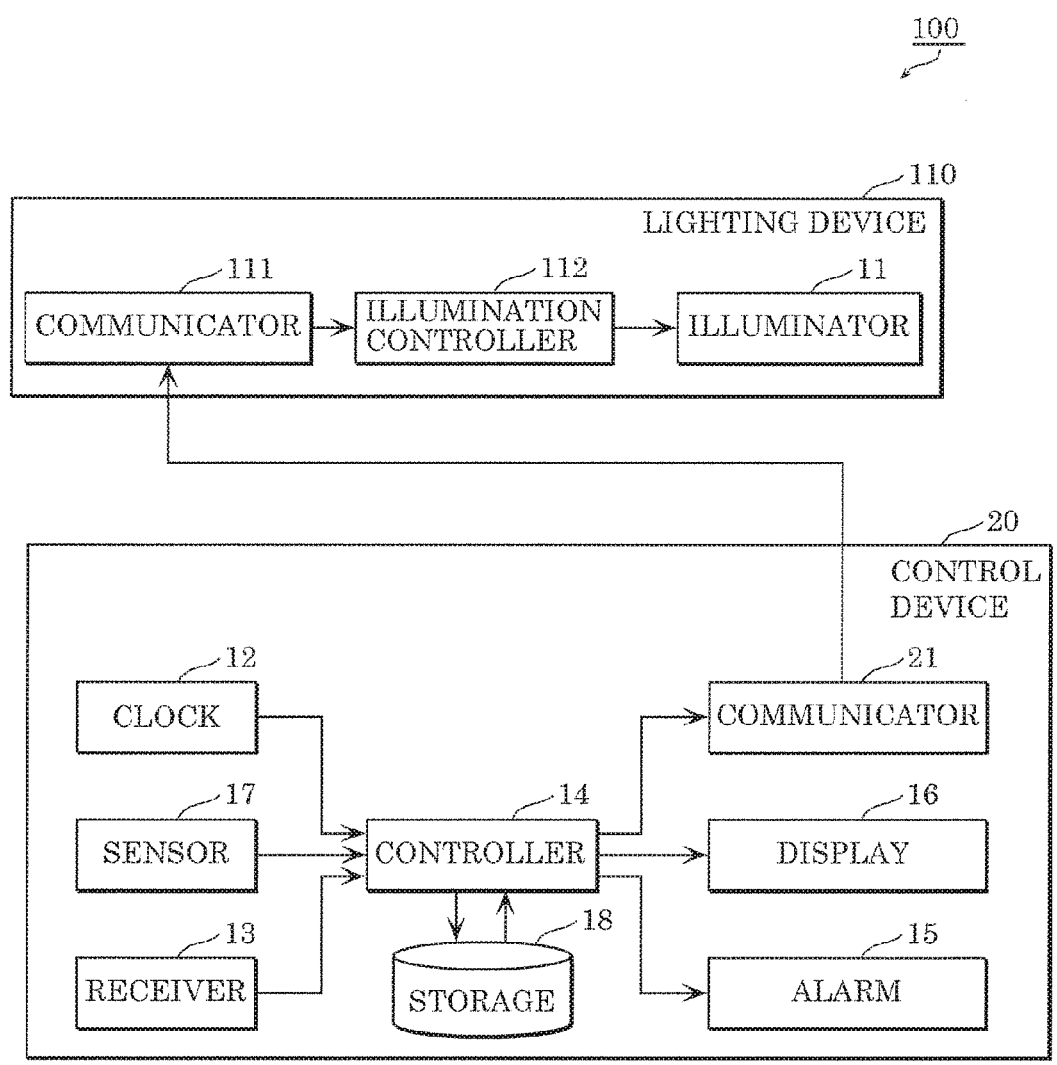
FIG. 16 is a block diagram illustrating a functional configuration of the lighting system according to Embodiment 2.

FIG. 15 is a schematic diagram illustrating a configuration and a use environment of lighting system 100 according to the present embodiment. FIG. 16 is a block diagram illustrating a functional configuration of lighting system 100 according to the present embodiment.

As illustrated in FIGS. 15 and 16, lighting system 100 includes lighting device 110 and control device 20 which controls lighting device 110. Lighting device 110 is a desk-lamp lighting device as with Embodiment 1. Control device 20 is a mobile terminal such as a smartphone.

As illustrated in FIG. 16, control device 20 includes clock 12, receiver 13, controller 14, alarm 15, display 16, sensor 17, storage 18, and communicator 21. In other words, control device 20 includes the elements of lighting device 10 according to Embodiment 1 except for illuminator 11. Lighting device 110 includes illuminator 11, communicator 111, and lighting controller 112.

Communicators 21 and 111 communicate with one another. In the present embodiment, communicators 21 and 111 wirelessly communicate with one another. Any type of wireless communication may be used, such as Bluetooth (registered trademark), Wi-Fi (registered trademark), Zigbee (registered trademark), and infrared ray communication, for example. Note that communicators 21 and 111 are connected with a wire such as a cable, and wired communication via the cable may be established between the communicators.

Lighting controller 112 controls the dimming and the color of illuminator 11, based on a control signal transmitted from controller 14 of control device 20.

As described above, lighting system 100 according to the present embodiment includes lighting device 110 which includes illuminator 11 which emits illumination light, control device 20 which controls lighting device 110, sensor 17 which detects whether an eye of user 1 is open. Control device 20 includes clock 12 which measures time, receiver 13 which receives input of a set time from user 1, and controller 14 which controls, at or after the set time, the dimming level of illuminator 11, in accordance with a control pattern based on the result of detection by sensor 17.

In this manner, lighting device 110 may change the dimming level of illuminator 11, based on control of control device 20. Thus, for example, wake-up control described in Embodiment 1 can be performed using an existing lighting device (light) which has a communication function and a dimming function. User 1 can be pleasantly woken up by efficient use of the existing lighting device.

Figure 17:
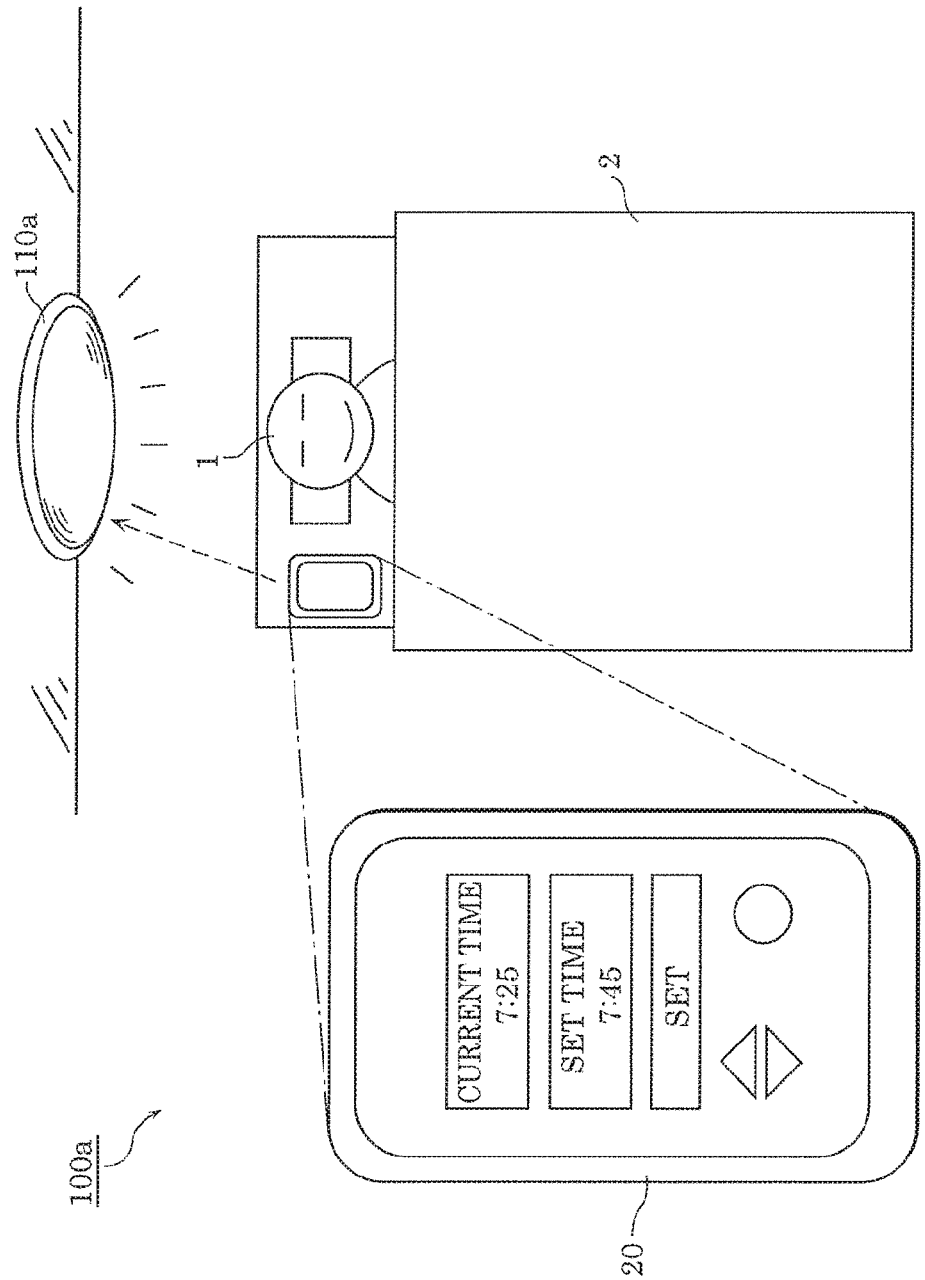
FIG. 17 is a schematic diagram illustrating a lighting system according to a variation of Embodiment 2 and a use environment of the lighting system.

Note that the present embodiment has described an example in which lighting device 110 is a desk-lamp lighting device, but lighting device 110 is not limited to such a lighting device. FIG. 17 is a schematic diagram illustrating lighting system 100a according to a variation of the present embodiment and a use environment of lighting system 100a.

Lighting device 110a according to this variation is a lighting device installed on a ceiling, and is a ceiling light, for example. In this variation, user 1 inputs a set time, for instance, via receiver 13 of control device 20. In other words, lighting device 110a does not need to include an input button, for instance, and thus user 1 does not need to touch lighting device 110a. Accordingly, even if a lighting device is installed on the ceiling such as lighting device 110a, user 1 may operate control device 20 at hand, and thus user convenience is not impaired. Furthermore, by emitting illumination light from lighting device 110a provided on the ceiling, the illumination light readily fall on the face of user 1.

Note that lighting device 110a may be, for instance, a downlight, a spotlight, a pendant light, a chandelier, a bracket light, or a footlight, rather than a ceiling light.

Embodiment 3

The following describes a lighting system according to Embodiment 3. In Embodiment 2, the control device controls one lighting device, whereas in a lighting system according to the present embodiment, a control device controls a plurality of lighting devices.

Figure 18:
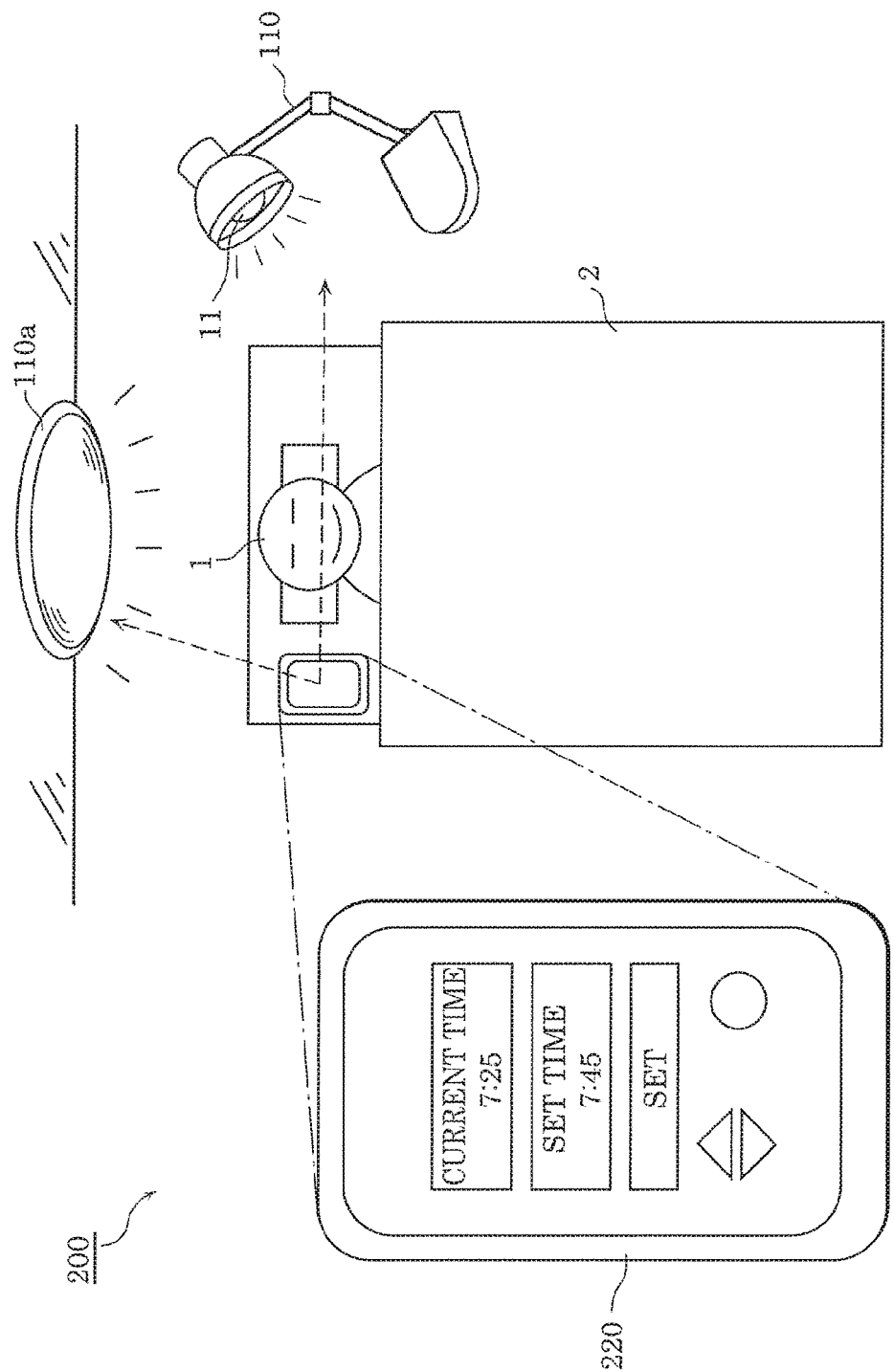
FIG. 18 is a schematic diagram illustrating a lighting system according to Embodiment 3 and a use environment of the lighting system.
Figure 19:
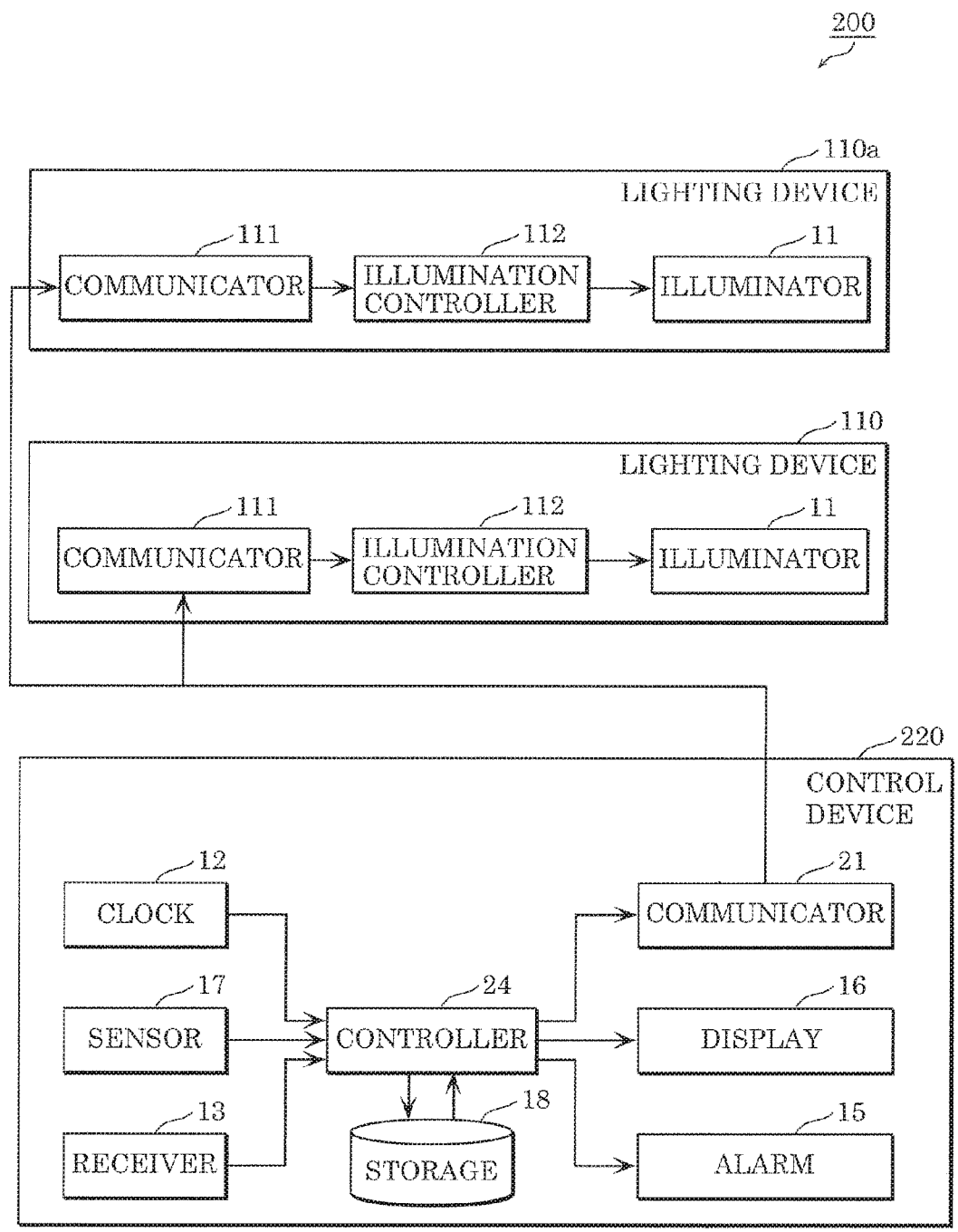
FIG. 19 is a block diagram illustrating a functional configuration of the lighting system according to Embodiment 3.

FIG. 18 is a schematic diagram illustrating a configuration and a use environment of lighting system 200 according to the present embodiment. FIG. 19 is a block diagram illustrating a functional configuration of lighting system 200 according to the present embodiment.

As illustrated in FIGS. 18 and 19, lighting system 200 includes lighting device 110, lighting device 110a, and control device 220 which controls lighting devices 110 and 110a. Note that since lighting devices 110 and 110a are the same as the lighting device according to Embodiment 2, and thus a description thereof is omitted.

As illustrated in FIG. 19, control device 220 is different from control device 20 according to Embodiment 2 in that controller 24 is included instead of controller 14. Specifically, controller 24 causes lighting device 110a to perform gradual increase control of the wake-up control, and causes lighting device 110 to perform awakening control of the wake-up control. In other words, controller 24 transmits designation of a dimming level for gradual increase control via communicator 21 to lighting device 110a. Controller 24 transmits designation of a dimming level for awakening control via communicator 21 to lighting device 110.

As described above, control device 220 performs wake-up control using lighting devices 110 and 110a, thus pleasantly waking up user 1.

Note that in the present embodiment, lighting device 110 may perform gradual increase control, and lighting device 110a may perform awakening control. Alternatively, lighting devices 110 and 110a may each perform both gradual increase control and awakening control.

Embodiment 4

The following describes a lighting system according to Embodiment 4. Embodiment 3 above has described an example in which the control device includes an alarm, whereas in a lighting system according to the present embodiment, a speaker separate from a lighting device and a control device includes an alarm.

Figure 20:
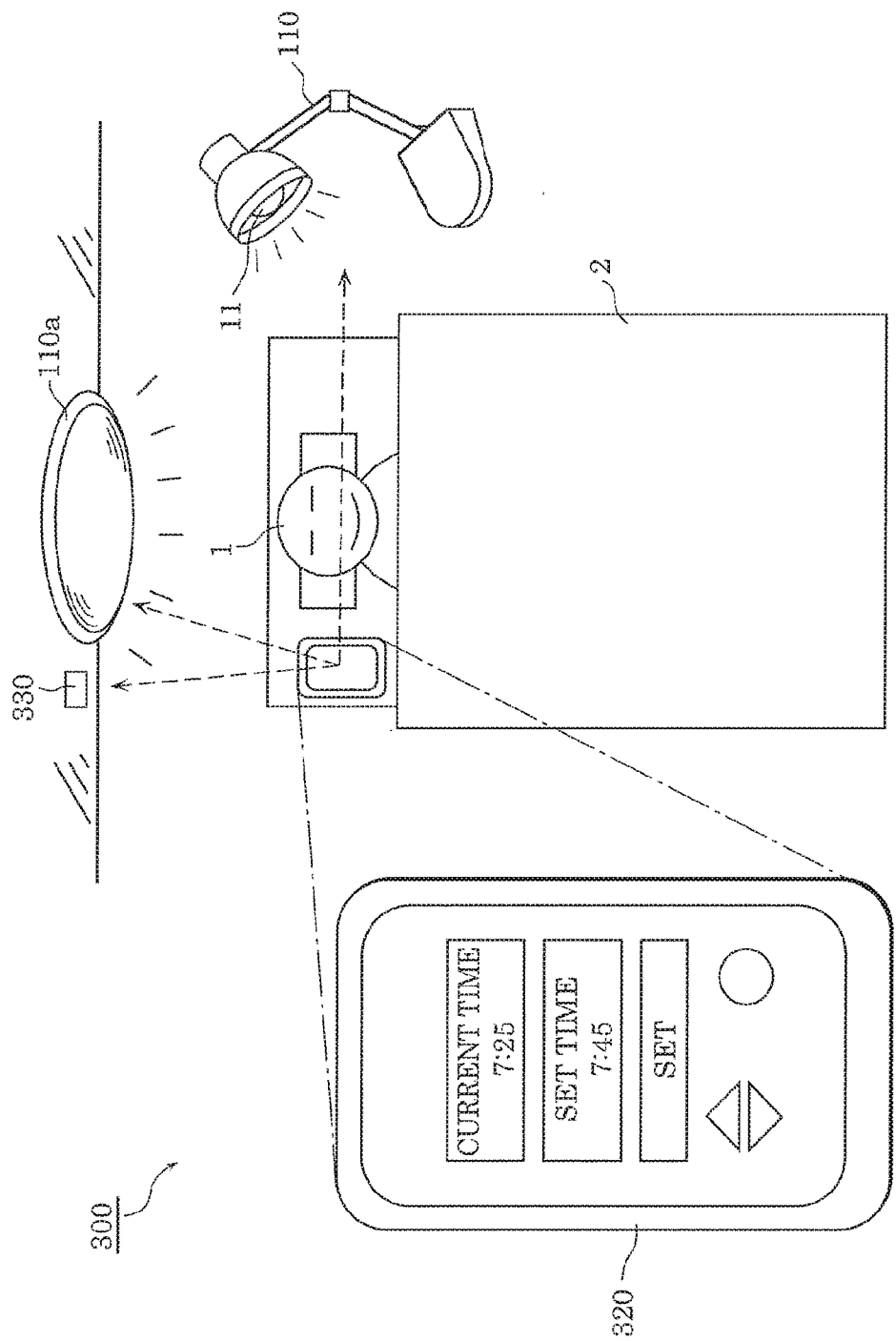
FIG. 20 is a schematic diagram illustrating a lighting system according to Embodiment 4 and a use environment of the lighting system.
Figure 21:
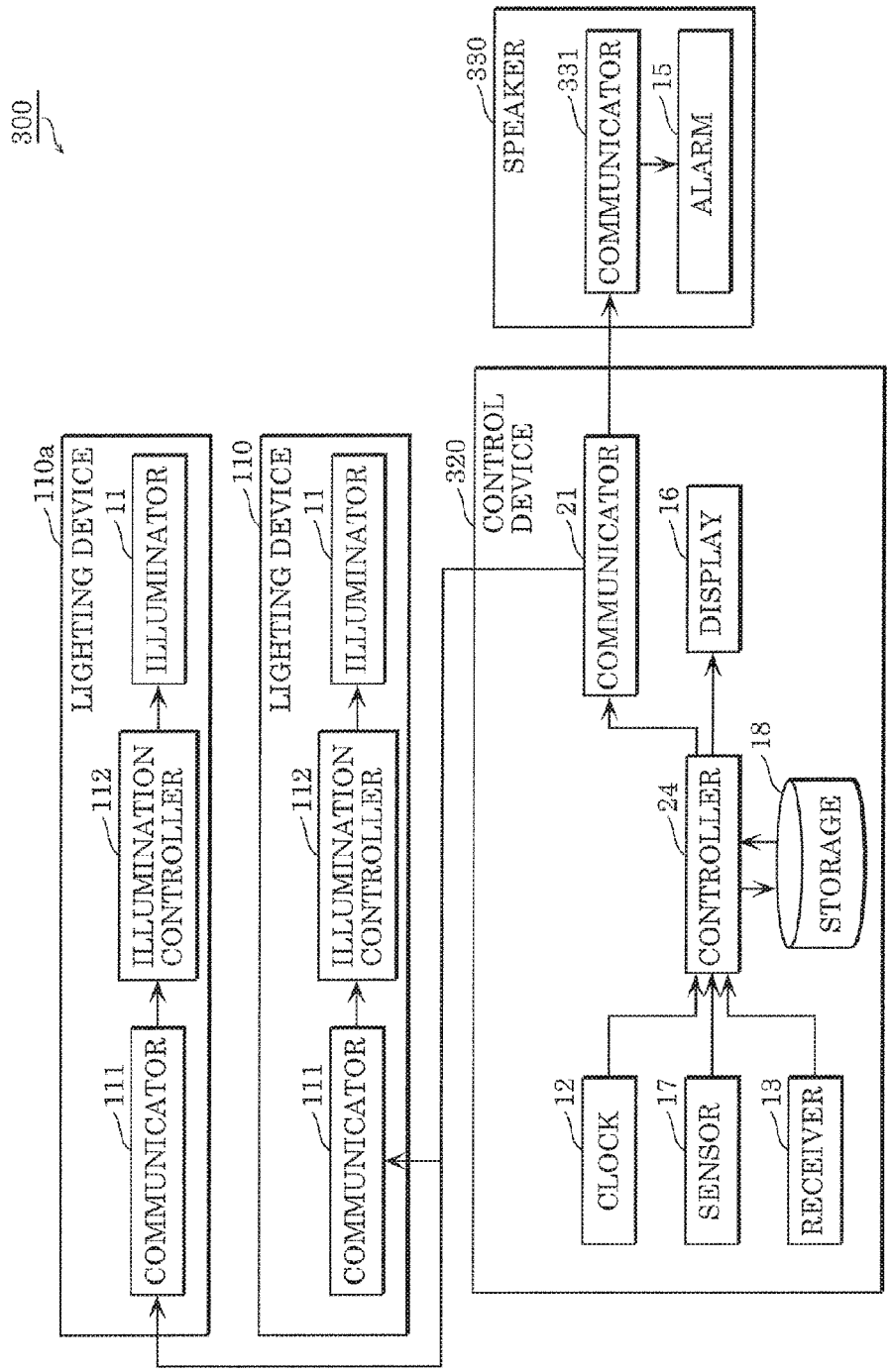
FIG. 21 is a block diagram illustrating a functional configuration of the lighting system according to Embodiment 4.

FIG. 20 is a schematic diagram illustrating lighting system 300 according to the present embodiment and a use environment of lighting system 300. FIG. 21 is a block diagram illustrating a functional configuration of lighting system 300 according to the present embodiment.

As illustrated in FIGS. 20 and 21, lighting system 300 includes lighting device 110, lighting device 110a, speaker 330, and control device 320 which controls lighting devices 110 and 110a and speaker 330. Lighting device 110 and lighting device 110a are the same as the lighting device according to Embodiment 3, and thus a description thereof is omitted.

As illustrated in FIG. 21, control device 320 is different from control device 220 according to Embodiment 3 in that alarm 15 is not included. Control device 320 does not include alarm 15, and thus controller 24 causes speaker 330 to emit alarm sound by controlling speaker 330 via communicator 21. Timing for emitting alarm sound is the same as that of Embodiment 1.

In the present embodiment, speaker 330 is a speaker directly attached to the ceiling, as illustrated in FIG. 20, but is not limited to such a speaker. For example, if an audio system and TV, for instance, are placed near bed 2 (in a bedroom), these can also be used as speaker 330.

Speaker 330 includes communicator 331 and alarm 15 as illustrated in FIG. 21. Communicator 331 communicates with communicator 21. Communication between communicators 331 and 21 is established wirelessly, for example. Specifically, wireless communication is Bluetooth (registered trademark), Wi-Fi (registered trademark), Zigbee (registered trademark), or infrared ray communication, for instance.

Alarm 15 produces alarm sound based on a control signal transmitted from controller 24 of control device 320 via communicators 21 and 331.

As described above, alarm sound can also be emitted using speaker 330 separate from control device 320 and lighting devices 110 and 110a.

Others

The above has described the lighting device and the lighting system according to the present disclosure, based on the embodiments and the variations thereof. Nevertheless, the present disclosure is not limited to such embodiments.

For example, in the above embodiment, a temporal change in the dimming level is fitted to a sigmoid curve using the least square method, but the method of fitting the change is not limited to this. Other general techniques used for curve fitting may be used.

The above embodiment has described an example in which first time T1 is a time at which alarm sound is stopped or a time when the alarm period has elapsed, but is not limited such times. First time T1 may be the set time. Thus, controller 14 may decrease the dimming level during a period when alarm sound is being produced. In the awakening control in second or subsequent iterations, first time T1 may be a time when previous awakening control has ended.

The above embodiment has described an example in which second time T2 is a time at which the dimming level has reached the first target value (dimming level Y2), but second time T2 is not limited to such a time. Second time T2 may be a time after a predetermined period has elapsed since first time T1. Thus, during awakening control, controller 14 may decrease the dimming level over a predetermined period, rather than until the dimming level reaches the first target value.

For example, in the above embodiment, during awakening control, the dimming level is maintained from third time T3 to fourth time T4, but may not be maintained. Controller 14 may iterate awakening control again, without maintaining the dimming level. In other words, third time T3 may be first time T1 in the subsequent awakening control. Controller 14 may not iterate awakening control and perform awakening control only once.

The above embodiment has described an example in which lighting device 10 or lighting system 100, for instance, includes alarm 15, but may not include alarm 15. For example, alarm sound may not be produced at the set time.

For example, in the above embodiment, controller 14 changes the correlated color temperature of illumination light according to a change in the dimming level from second time T2 to third time T3, but may not change the correlated color temperature. For example, illuminator 11 may not have a color control function, and the correlated color temperature of the illumination light may be constant at all times. Alternatively, controller 14 may change the correlated color temperature of the illumination light, over a period from first time T1 to second time T2, or may change the correlated color temperature of the illumination light in gradual increase control.

The above embodiment has described an example in which lighting device 10 or control device 20, for instance, includes sensor 17, but lighting device 10 or control device 20 may not include sensor 17. Sensor 17 may be provided separately from lighting device 10 and control device 20, for instance.

Similarly, an example in which lighting device 10 or control device 20, for instance, includes display 16 has been described, but lighting device 10 or control device 20 may not include display 16. Display 16 may be provided separately from lighting device 10 and control device 20, for instance.

The above embodiment has described an example in which wake-up control includes gradual increase control and awakening control, but wake-up control may not include both. For example, wake-up control may include only awakening control. Awakening control may not gradually increase or decrease the dimming level, and a high value (for example, maximum value) and a low value (for example, minimum value) may be switched alternately.

In the above embodiments, each of the elements may be configure of dedicated hardware or may be achieved by executing a software program appropriate for the element. The elements may be achieved by a program executor such as a central processing unit (CPU) or a processor reading and executing a software program stored in a recording medium such as a hard disk or semiconductor memory.

Note that the present disclosure is achieved not only as the lighting device and the lighting system, but also as a program which includes, as steps, the processing performed by the elements of the lighting device and the lighting system, and also as a computer-readable recording medium which stores the program such as a digital versatile disc (DVD).

Thus, these general and specific aspects described above may be implemented using a system, a device, an integrated circuit, a computer program, or a computer-readable recording medium, or any combination of systems, devices, integrated circuits, computer programs, and recording media.

The present disclosure may also include embodiments as a result of adding, to the embodiments, various modifications which may be conceived by those skilled in the art, and embodiments obtained by combining elements and functions in the embodiments in any manner as long as the combination does not depart from the scope of the present disclosure.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A lighting device comprising:
an illuminator which emits illumination light;
a clock which measures time;
a receiver which receives input of a set time from a user;
a detector which detects whether an eye of the user is open; and
a controller which controls, at or after the set time, a dimming level of the illuminator, in accordance with a control pattern based on a result of the detection by the detector, wherein:
when the detector does not detect that an eye of the user is open, the controller performs awakening control for decreasing the dimming level of the illuminator over a period from a first time at or after the set time to a second time, and increasing the dimming level over a period from the second time to a third time, and
the second time is a time when decreasing the dimming level ends and when increasing the dimming level starts.

2. The lighting device according to claim 1, wherein:
in the awakening control, the controller controls the dimming level from the second time to the third time, based on a function expressed by, using constants a, b, c, and d:

$$Y = d + \frac{a-d}{1+(t/c)^b}$$

where Y denotes the dimming level and t denotes time, and
the constant c is a value closer to the second time than the third time.

3. The lighting device according to claim 2, wherein the controller controls the dimming level of the illuminator at a maximum value after the detector detects that an eye of the user is open.

4. The lighting device according to claim 3, wherein:
the controller performs open-eye control for increasing the dimming level to the maximum value when the detector detects that an eye of the user is open, and
the controller controls the diming level in the open-eye control, based on the function, and
the constant c of the function during the open-eye control is a value closer to a time at which the dimming level reaches the maximum value than a time at which the open-eye control starts.

5. The lighting device according to claim 2, wherein the controller iterates the awakening control when the detector does not detect that an eye of the user is open.

6. The lighting device according to claim 5, wherein during the awakening control, the controller further maintains a dimming level at the third time, from the third time to a fourth time.

7. The lighting device according to claim 2, further comprising
an alarm which emits alarm sound, wherein
during the awakening control, the controller further causes the alarm to emit the alarm sound at the third time.

8. The lighting device according to claim 7, wherein
in iteration of the awakening control, the controller intermittently causes the alarm to emit the alarm sound at the third time.

9. The lighting device according to claim 2, wherein
the controller further performs gradual increase control for causing the illuminator to start emitting the illumination light at a start time prior to the set time, and gradually increasing the dimming level until the set time.

10. A lighting system comprising:
a lighting device which includes an illuminator which emits illumination light;
a control device which controls the lighting device; and
a detector which detects whether an eye of a user is open, wherein the control device includes:

a clock which measures time;

a receiver which receives input of a set time from the user; and a controller which controls, at or after the set time, a dimming level of the illuminator, in accordance with a control pattern based on a result of the detection by the detector, wherein:

when the detector does not detect that an eye of the user is open, the controller performs awakening control for decreasing the dimming level of the illuminator over a period from a first time at or after the set time to a second time, and increasing the dimming level over a period from the second time to a third time, and the second time is a time when decreasing the dimming level ends and when increasing the dimming level starts.

* * * * *